(12) United States Patent
Sanchez

(10) Patent No.: US 8,677,996 B2
(45) Date of Patent: Mar. 25, 2014

(54) VENTILATION SYSTEM WITH SYSTEM STATUS DISPLAY INCLUDING A USER INTERFACE

(75) Inventor: Gabriel Sanchez, Valley Center, CA (US)

(73) Assignee: Covidien LP, Mansfield, MA (US)

( * ) Notice: Subject to any disclaimer, the term of this patent is extended or adjusted under 35 U.S.C. 154(b) by 324 days.

(21) Appl. No.: 12/775,793

(22) Filed: May 7, 2010

(65) Prior Publication Data
US 2011/0132362 A1 Jun. 9, 2011

Related U.S. Application Data

(60) Provisional application No. 61/266,731, filed on Dec. 4, 2009.

(51) Int. Cl.
A62B 7/00 (2006.01)

(52) U.S. Cl.
USPC ............ 128/204.21; 128/204.18; 128/200.24; 128/205.23

(58) Field of Classification Search
USPC .................. 128/200.24, 201.27, 204.18, 128/204.21–204.24, 205.23, 903; 345/1.1–3.1, 156, 173, 204–205, 345/211–215, 904; 715/700, 716
See application file for complete search history.

(56) References Cited

U.S. PATENT DOCUMENTS

| 4,227,645 A | 10/1980 | de La Farge et al. |
| 4,323,064 A | 4/1982 | Hoenig et al. |
| 4,625,843 A | 12/1986 | Maltby et al. |
| 4,720,709 A | 1/1988 | Imamura et al. |
| 4,752,089 A | 6/1988 | Carter |
| 4,921,642 A | 5/1990 | LaTorraca |
| 4,954,799 A | 9/1990 | Kumar |
| 4,991,576 A | 2/1991 | Henkin et al. |
| 5,038,792 A | 8/1991 | Mault |
| 5,057,822 A | 10/1991 | Hoffman |
| 5,072,360 A | 12/1991 | Knorpp et al. |
| 5,072,737 A | 12/1991 | Goulding |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |

(Continued)

FOREIGN PATENT DOCUMENTS

| JP | 08141085 | 4/1996 |
| WO | WO2005/013879 | 2/2005 |

(Continued)

OTHER PUBLICATIONS

PCT International Search Report and Written Opinion in International Application PCT/US2011/033460 mailed Oct. 12, 2011, 17 pgs.

(Continued)

*Primary Examiner* — Loan Thanh
*Assistant Examiner* — Joshua Lee

(57) ABSTRACT

The disclosure describes a novel approach for displaying information on a ventilator system. The disclosure describes a novel respiratory system including a removable primary display and system status display. Further, the disclosure describes a novel method for displaying ventilator information and a novel method for controlling a ventilator system.

19 Claims, 14 Drawing Sheets

(56) References Cited

U.S. PATENT DOCUMENTS

| | | |
|---|---|---|
| 5,301,921 A | 4/1994 | Kumar |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,372,545 A | 12/1994 | Noda et al. |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,452,714 A | 9/1995 | Anderson et al. |
| 5,503,145 A | 4/1996 | Clough |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,542,415 A | 8/1996 | Brady |
| 5,544,674 A | 8/1996 | Kelly |
| 5,549,106 A | 8/1996 | Gruenke et al. |
| 5,570,688 A | 11/1996 | Cochran et al. |
| 5,590,648 A | 1/1997 | Mitchell et al. |
| 5,596,984 A | 1/1997 | O'Mahony et al. |
| 5,611,327 A | 3/1997 | Teixeira Filho et al. |
| 5,630,411 A | 5/1997 | Holscher |
| 5,632,270 A | 5/1997 | O'Mahony et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,678,539 A | 10/1997 | Schubert et al. |
| 5,687,717 A | 11/1997 | Halpern et al. |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,899,204 A | 5/1999 | Cochran |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,931,160 A | 8/1999 | Gilmore et al. |
| 5,934,274 A | 8/1999 | Merrick et al. |
| 5,991,883 A | 11/1999 | Atkinson |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahoney et al. |
| 6,158,432 A | 12/2000 | Biondi et al. |
| 6,158,433 A | 12/2000 | Ong et al. |
| 6,161,539 A | 12/2000 | Winter |
| 6,178,905 B1 | 1/2001 | Dynes et al. |
| 6,220,245 B1 | 4/2001 | Takabayashi et al. |
| 6,269,812 B1 | 8/2001 | Wallace et al. |
| 6,273,088 B1 | 8/2001 | Hillsman |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,327,482 B1 | 12/2001 | Miyashita |
| 6,349,724 B1 | 2/2002 | Burton et al. |
| 6,357,438 B1 | 3/2002 | Hansen |
| 6,360,745 B1 | 3/2002 | Wallace et al. |
| 6,363,404 B1 | 3/2002 | Dalal et al. |
| 6,369,838 B1 | 4/2002 | Wallace et al. |
| 6,390,091 B1 | 5/2002 | Banner et al. |
| 6,392,158 B1 | 5/2002 | Caplet et al. |
| 6,412,483 B1 | 7/2002 | Jones et al. |
| 6,439,229 B1 | 8/2002 | Du et al. |
| 6,463,930 B2 | 10/2002 | Biondi et al. |
| 6,467,478 B1 | 10/2002 | Merrick et al. |
| 6,512,938 B2 | 1/2003 | Claure et al. |
| 6,515,683 B1 | 2/2003 | Wright |
| 6,517,492 B2 | 2/2003 | Koblanski |
| 6,543,449 B1 | 4/2003 | Woodring et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,591,835 B1 | 7/2003 | Blanch |
| 6,597,939 B1 | 7/2003 | Lampotang et al. |
| 6,622,726 B1 | 9/2003 | Du |
| 6,644,310 B1 | 11/2003 | Delache et al. |
| 6,668,824 B1 | 12/2003 | Isaza et al. |
| 6,670,950 B1 | 12/2003 | Chin et al. |
| 6,671,529 B2 | 12/2003 | Claure et al. |
| 6,675,801 B2 | 1/2004 | Wallace et al. |
| 6,686,716 B1 | 2/2004 | Predina et al. |
| 6,718,974 B1 | 4/2004 | Moberg |
| 6,725,447 B1 | 4/2004 | Gilman et al. |
| 6,738,079 B1 | 5/2004 | Kellarman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,782,888 B1 | 8/2004 | Friberg et al. |
| 6,796,305 B1 | 9/2004 | Banner et al. |
| 6,814,074 B1 | 11/2004 | Nadjafizadeh et al. |
| 6,834,647 B2 | 12/2004 | Blair et al. |
| 6,837,242 B2 | 1/2005 | Younes |
| 6,860,266 B2 | 3/2005 | Blike |
| 6,866,040 B1 | 3/2005 | Bourdon |
| 6,899,103 B1 | 5/2005 | Hood et al. |
| 6,956,572 B2 | 10/2005 | Zaleski |
| 6,960,854 B2 | 11/2005 | Nadjafizadeh et al. |
| 7,013,435 B2 | 3/2006 | Gallo et al. |
| 7,017,574 B2 | 3/2006 | Biondi et al. |
| 7,036,504 B2 | 5/2006 | Wallace et al. |
| 7,039,878 B2 | 5/2006 | Auer et al. |
| 7,040,057 B2 | 5/2006 | Gallant et al. |
| 7,040,318 B2 | 5/2006 | Dascher et al. |
| 7,040,321 B2 | 5/2006 | Gobel |
| 7,043,585 B2 | 5/2006 | Okin |
| 7,044,930 B2 | 5/2006 | Stromberg |
| 7,047,092 B2 | 5/2006 | Wimsatt |
| 7,062,251 B2 | 6/2006 | Birkett et al. |
| 7,077,131 B2 | 7/2006 | Hansen |
| RE39,225 E | 8/2006 | Isaza et al. |
| 7,117,438 B2 | 10/2006 | Wallace et al. |
| 7,162,296 B2 | 1/2007 | Leonhardt et al. |
| 7,188,621 B2 * | 3/2007 | DeVries et al. ......... 128/204.21 |
| 7,201,166 B2 | 4/2007 | Blaise et al. |
| 7,210,478 B2 | 5/2007 | Banner et al. |
| 7,220,365 B2 | 5/2007 | Qu et al. |
| 7,255,103 B2 | 8/2007 | Bassin |
| 7,270,126 B2 | 9/2007 | Wallace et al. |

(56) References Cited

U.S. PATENT DOCUMENTS

| | | |
|---|---|---|
| 7,290,544 B1 | 11/2007 | Särelä et al. |
| 7,334,578 B2 | 2/2008 | Biondi et al. |
| 7,362,341 B2 | 4/2008 | McGuire et al. |
| 7,369,757 B2 | 5/2008 | Farbarik |
| 7,370,650 B2 | 5/2008 | Nadjafizadeh et al. |
| 7,395,216 B2 | 7/2008 | Rosenfeld et al. |
| 7,419,469 B2 | 9/2008 | Vacca |
| 7,428,902 B2 | 9/2008 | Du et al. |
| 7,433,827 B2 | 10/2008 | Rosenfeld et al. |
| 7,454,359 B2 | 11/2008 | Rosenfeld et al. |
| D583,948 S | 12/2008 | Hachimaru et al. |
| 7,460,959 B2 | 12/2008 | Jafari |
| 7,487,773 B2 | 2/2009 | Li |
| 7,502,221 B2 | 3/2009 | Fuller |
| 7,530,353 B2 | 5/2009 | Choncholas |
| 7,654,802 B2 | 2/2010 | Crawford, Jr. et al. |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,997,269 B2 | 8/2011 | Yudkovitch et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0017299 A1 | 2/2002 | Hickle |
| 2002/0044059 A1 | 4/2002 | Reeder et al. |
| 2002/0080138 A1 | 6/2002 | Tarr |
| 2003/0062045 A1 | 4/2003 | Woodring et al. |
| 2003/0092381 A1 | 5/2003 | Buel et al. |
| 2003/0208465 A1 | 11/2003 | Yurko et al. |
| 2004/0030721 A1 | 2/2004 | Kruger et al. |
| 2004/0176983 A1 | 9/2004 | Birkett et al. |
| 2005/0016534 A1 | 1/2005 | Ost |
| 2005/0030309 A1 | 2/2005 | Gettman et al. |
| 2005/0039748 A1 | 2/2005 | Andrieux |
| 2005/0086612 A1 | 4/2005 | Gettman et al. |
| 2005/0108057 A1 | 5/2005 | Cohen et al. |
| 2005/0113668 A1 | 5/2005 | Srinivasan |
| 2005/0133027 A1 | 6/2005 | Elaz et al. |
| 2005/0139212 A1 | 6/2005 | Bourdon |
| 2005/0156933 A1 | 7/2005 | Lee et al. |
| 2005/0247311 A1 | 11/2005 | Vacchiano et al. |
| 2005/0288571 A1 | 12/2005 | Perkins et al. |
| 2006/0155183 A1 | 7/2006 | Kroecker et al. |
| 2006/0161748 A1 | 7/2006 | Wang et al. |
| 2006/0162727 A1* | 7/2006 | Biondi et al. ............ 128/204.21 |
| 2006/0178911 A1 | 8/2006 | Syed et al. |
| 2006/0264762 A1 | 11/2006 | Starr |
| 2007/0017515 A1 | 1/2007 | Wallace et al. |
| 2007/0062529 A1 | 3/2007 | Choncholas et al. |
| 2007/0062532 A1 | 3/2007 | Choncholas |
| 2007/0062533 A1 | 3/2007 | Choncholas et al. |
| 2007/0077200 A1 | 4/2007 | Baker |
| 2007/0185390 A1 | 8/2007 | Perkins et al. |
| 2007/0199566 A1 | 8/2007 | Be'eri |
| 2007/0227537 A1 | 10/2007 | Bemister et al. |
| 2007/0272242 A1 | 11/2007 | Sanborn et al. |
| 2007/0284361 A1 | 12/2007 | Nadjafizadeh et al. |
| 2008/0000479 A1* | 1/2008 | Elaz et al. ............... 128/204.23 |
| 2008/0053441 A1 | 3/2008 | Gottlib et al. |
| 2008/0072896 A1 | 3/2008 | Setzer |
| 2008/0072902 A1 | 3/2008 | Setzer |
| 2008/0078390 A1 | 4/2008 | Milne et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0110460 A1 | 5/2008 | Elaz et al. |
| 2008/0183057 A1 | 7/2008 | Taube |
| 2008/0236585 A1 | 10/2008 | Parker et al. |
| 2008/0281167 A1 | 11/2008 | Soderberg |
| 2008/0295830 A1 | 12/2008 | Martonen et al. |
| 2009/0005651 A1 | 1/2009 | Ward et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0234328 A1 | 9/2009 | Cox et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0018530 A1 | 1/2010 | Schindhelm et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0057618 A1 | 3/2010 | Spicer et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |

(56) References Cited

U.S. PATENT DOCUMENTS

| | | |
|---|---|---|
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0175728 A1 | 7/2011 | Baker, Jr. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |

FOREIGN PATENT DOCUMENTS

| | | |
|---|---|---|
| WO | WO2006/020862 | 2/2006 |
| WO | WO2007/111716 | 10/2007 |
| WO | WO2007/117716 A2 | 10/2007 |
| WO | WO 2009/120607 A1 | 10/2009 |

OTHER PUBLICATIONS

PCT International Search Report and Written Opinion mailed Jun. 16, 2011; International Application No. PCT/US2010/058850, 16 pages.

PCT International Search Report Date of Mailing Mar. 18, 2011, Applicant's File Reference No. H-RM-02015W0, International Application No. PCT/US2010/058850, International Filing Date Dec. 3, 2010.

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

U.S. Appl. No. 12/775,779, Office Action mailed Sep. 25, 2012, 20 pgs.

U.S. Appl. No. 12/775,788, Office Action mailed Sep. 25, 2012, 20 pgs.

U.S. Appl. No. 12/768,649, Office Action mailed Sep. 20, 2012, 12 pgs.

U.S. Appl. No. 29/299,059, Notice of Allowance emailed Nov. 23, 2011, 8 pgs.

U.S. Appl. No. 29/360,549, Notice of Allowance mailed May 10, 2011, 8 pgs.

U.S. Appl. No. 29/360,549, Notice of Allowance mailed Jun. 10, 2011, 3 pgs.

U.S. Appl. No. 12/775,779, Notice of Allowance mailed Dec. 18, 2012, 10 pgs.

U.S. Appl. No. 12/768,656, Notice of Allowance mailed Jan. 28, 2013, 8 pgs.

U.S. Appl. No. 12/768,569, Notice of Allowance mailed Feb. 5, 2013, 8 pgs.

U.S. Appl. No. 12/768,649, Office Action mailed Feb. 12, 2013, 11 pgs.

U.S. Appl. No. 12/768,656, Notice of Allowance mailed Mar. 25, 2013, 2 pgs.

U.S. Appl. No. 12/768,569, Notice of Allowance mailed Mar. 25, 2013, 2 pgs.

U.S. Appl. No. 12/768,569, Notice of Allowance mailed Apr. 23, 2013, 2 pgs.

U.S. Appl. No. 12/768,649, Notice of Allowance mailed May 17, 2013, 6 pgs.

U.S. Appl. No. 12/768,656, Notice of Allowance mailed May 3, 2013, 2 pgs.

U.S. Appl. No. 12/768,569, Notice of Allowance mailed May 6, 2013, 2 pgs.

U.S. Appl. No. 12/768,656, Notice of Allowance mailed Jul. 19, 2013, 2 pgs.

Drager Medical, Instructions for Use Infinity Acute Care System, Evita Infinity V500 Ventilation Unit SW 1.n, 1st edition, Jun. 2008, Drager Medical, Germany, 276 pgs.

\* cited by examiner

VENTILATION SYSTEM WITH SYSTEM STATUS DISPLAY INCLUDING A USER INTERFACE

RELATED APPLICATION

This application claims the benefit of U.S. Provisional Application No. 61/266,731, filed Dec. 4, 2009, and entitled "Ventilation System Status Display", which application is hereby incorporated herein by reference.

INTRODUCTION

Many devices now use electronic graphical user interfaces (GUIs) as the primary user interface means instead of panels with mechanical elements such as knobs, buttons, switches etc. These GUIs are typically presented on a suitably-sized display (such as a flat panel display) in conjunction with a pointing or, as is increasingly common, a touch-sensitive display.

One drawback of such devices, however, is a reliance on the display for both control of the primary function of the device and monitoring of the performance of the device. This allows, under certain circumstances, for a failure of the display electronics that does not affect the performance of the device to cause the operator of the device to be unable to determine if the device is still operational.

Another drawback of electronic GUIs is the power consumption the displays require. Large and high resolution displays and support circuitry often consume excessive amounts of power, making them unattractive for use with battery-powered devices.

Yet another drawback related to the power consumption issue is that in order for an operator to interact with or obtain information from the device in any way, the electronic GUI must be powered on, even when the information needed is unrelated to the operation of the device. For example, a device may have a battery that can be charged from wall power when the device is turned off. If the electronic GUI is the only interface, then in order to simply determine the charge condition of the battery, the device must be turned on in order to power the electronic GUI.

One way that has been used to address this problem is to provide combinations of limited function alpha numeric displays, lamps and LEDs in addition to the primary display to manage ancillary or status information that should be provided to the operator. However, such ancillary user interface elements can not be reconfigured as they are built into their devices. Therefore, if different operators want to see different types of ancillary information, the only way to achieve this is to create different physical housings for each set of ancillary information desired by consumers.

SUMMARY

The disclosure describes a novel approach for displaying information on a ventilator system. The disclosure describes a novel respiratory system including a removable primary display and system status display. Further, the disclosure describes a novel method for displaying ventilator information and a novel method for controlling a ventilator system.

In part, this disclosure describes a method for controlling a ventilator system. The method includes performing the following steps:

a) ventilating a patient with a ventilator system comprising a system status display and a primary display removable from a main ventilator housing;

b) controlling the system status display with a ventilation control system, wherein the ventilation control system receives and executes user selected secondary commands from the system status display;

c) controlling the primary display with a primary display controller, wherein the primary display controller receives and executes user selected primary commands from the primary display; and d) operating the system status display on less power than the amount of power necessary to operate the primary display.

Yet another aspect of this disclosure describes a ventilation system that includes: a main housing; a gas delivery system in the main housing; a ventilation control system in the main housing that controls the gas delivery system and monitors one or more of a patient physiological parameter, operational parameters of the ventilation system, and user-settable parameters; a primary display controller that generates a graphical user interface and that receives user inputs through the graphical user interface and capable of delivering primary commands to the ventilation control system based on the user inputs; a primary display housing removably attached to the main housing; a primary display in the primary display housing that presents the graphical user interface; and a system status display incorporated into the main housing that displays status data received from the ventilation control system and through which secondary commands may be input directly to the ventilation control system, wherein the secondary commands available are selected based on a status of the ventilation system, a current power source, a status of the primary display controller, a status of the primary display housing and a status of the primary display.

In yet another aspect, the disclosure describes a method for displaying ventilator information. This method includes performing the following steps:

a) controlling a system status display with a ventilation control system, wherein the ventilation control system receives and executes user selected secondary commands from the system status display;

b) controlling a primary display with a primary display controller, wherein the primary display controller receives and executes user selected primary commands from the primary display; and c) operating a system status display on less power than the amount of power necessary to operate a primary display controller.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments systems and methods described below and are not meant to limit the scope of the invention in any manner, which scope shall be based on the claims appended hereto.

DETAILED DESCRIPTION

Figure 1:
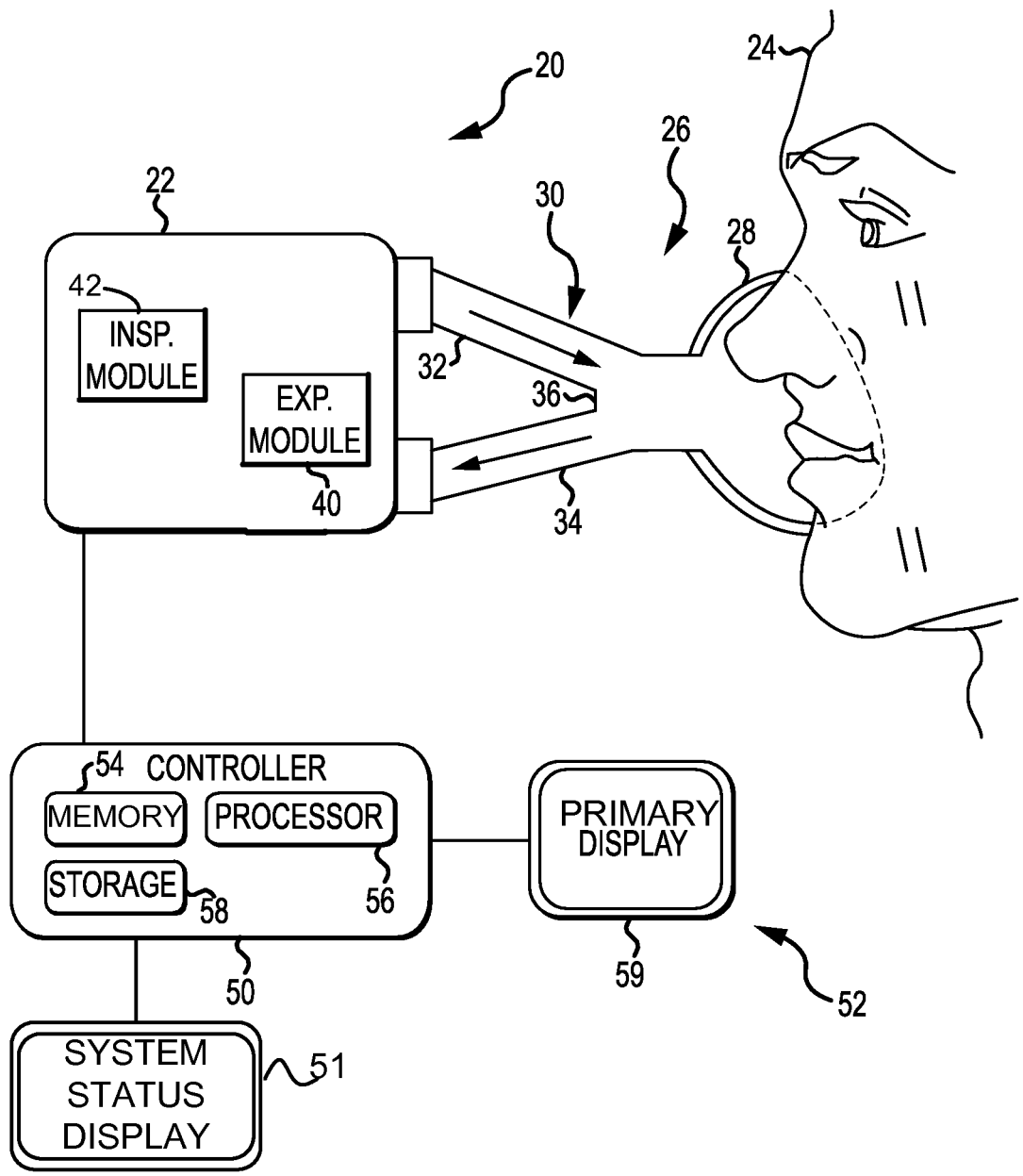
FIG. 1 illustrates an embodiment of a ventilator system including a primary removable display and a system status display.

This disclosure describes embodiments of a system status display for use in devices such as medical ventilators that have an electronic GUI on a primary display device. The system status display (SSD) is a secondary display that has a more limited functionality than the electronic GUI on the primary display, and is provided primarily, if not solely, for the purpose of providing system status information to the operator.

Although the technology introduced above and discussed in detail below may be implemented for a variety of devices (and not just medical devices), the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients, different types of medical devices and any devices that use an electronic GUI presented on a primary display.

Medical ventilators are used to provide mixed gases that can be delivered in different modes of operation to a patient who may otherwise be unable to breathe sufficiently. This could include assisting a weakly breathing patient by reducing the work of breathing or by breathing for a patient that is unable to breathe. In modern medical facilities, pressurized air and oxygen sources are often available from wall outlets. Other, exotic gases such as helium, helium-oxygen mixtures (heliox), nitrogen and argon to name but a few, may also be used depending on the therapy being administered.

Medical ventilators monitor the delivery of breathing gas to the patient, may directly or indirectly monitor physiological parameters of the patient, and monitor the operation of the ventilator.

In the embodiments described herein, operators control the medical interface through an electronic GUI presented on a primary display, possibly in conjunction with one or more user input devices such as a thumbwheel, mouse, keyboard, or selector. As described above, typically such a primary display is a large display which may be provided with touchscreen capability. The electronic GUI presented to the operator via this display allows the operator to view patient data in different forms, historical data, control the operation of the ventilator and change the therapy being provided to the patient. In an embodiment, every ventilator operation that can be performed by the ventilator can be accessed via the electronic GUI.

Because of the computing power necessary to drive such a primary display, a separate GUI controller (which may alternatively be referred to as the primary display controller or graphics subsystem) is often used that is solely dedicated to running the primary display, interpreting user inputs received through the GUI, and passing that information on to the main ventilator controller that controls the actual gas delivery operations of the ventilator and any subsystems within the ventilator. Another function is to perform the computations and manipulations necessary to raw data provided by the main ventilator controller or discreet ventilator subsystems and turn them into the graphical presentations (waveforms, loops, monitored patient data, average values, etc.) shown on the GUI. For example, in an embodiment, the main ventilator controller monitors and outputs current parameters, which are then stored in memory to be accessed as needed by the GUI controller.

An example of one such subsystem is a battery control system. Typically, medical ventilators may be provided with one or more batteries to allow the ventilator to remain in operation without interruption while a patient is being transported between locations or during power loss. The battery system may include a monitoring and recharging subsystem that monitors the charge state and performance of the battery or batteries and keeps the batteries in a charged state.

Depending on the configuration of the ventilator other subsystems may be provided such as modules associated with gas sources, e.g., that monitor the amount of gas remaining in a storage bottle or which gas sources are currently in use or modules associated with power management such as whether power is being delivered from a wall outlet or the battery system.

The SSD of the present disclosure is a secondary display that provides limited status information to the operator. In an embodiment, the SSD may not be interactive in any way, rather only providing status information in a predetermined or preselected format. Alternatively, some limited interaction may be provided through which a limited set of commands may be provided directly to the main breath delivery controller.

The SSD may be completely independent of the primary display and the GUI controller. One benefit of this is that either the primary display or the GUI controller could fail completely but the SSD would still provide the operator with information, obtained directly from the main ventilator controller, describing the performance of the ventilator. Another benefit of this architecture is that it allows the primary display and, thus the GUI, to be powered down or even completely removed from the ventilator while continuing to provide the user status of gas delivery to the patient and system status. Removal of the primary display allows for easy transport of the ventilator (as primary displays are often large and consume high amounts of power) without interrupting the delivery of respiratory therapy to a patient. Having the SSD operational when the primary display is powered down also has the benefit of allowing an operator to determine the status of various subsystems without the need to power up/boot up the GUI controller or other non-essential systems.

In an embodiment, the SSD is a display located on the breathe delivery housing that is always powered on and displaying status information when the ventilator is provided with external power, e.g., when it is plugged into a wall socket. In one embodiment, the SSD is a small, low-power display such as an LCD display to reduce the power demand of the SSD. The SSD may or may not be always powered on when the ventilator is under battery power. In an embodiment, when the ventilator is on battery power the SSD may power off and may be turned on using a separate SSD power switch (different from that controlling the primary display and electronic GUI). The SSD or drive circuitry may be able to determine when the primary display is turned off or removed during ventilation (e.g., such as for transport to conserve battery life) and may automatically turn on and remain on in such circumstances.

In an embodiment, when the SSD is on, the SSD may be programmable by the operator or manufacturer to meet local requirements or preferences. Likewise, the status data (that is data obtained from systems other than the GUI controller) displayed and the format of that display may also be user selectable.

FIG. 1 illustrates an embodiment of a ventilator system 20 (also referred to as ventilator 20) including a primary removable display 59, a system status display 51, a controller 50, and a pneumatic system 22 (also referred to as a gas delivery system 22). The ventilator system 20 further includes a main housing.

Ventilator 20 is connected to a human patient 24. Pneumatic system 22 (also referred to as a gas delivery system 22) delivers breathing gases to a patient 24 via the ventilation tubing system 26, which couples patient 24 to the pneumatic system 22 via physical patient interface 28 and ventilator circuit 30. The gas delivery system 22 is located in the main housing of ventilator 20. Ventilator circuit 30 could be a two-limb or one-limb circuit 30 for carrying gas mixture to and from the patient 24. In a two-limb embodiment as shown, a wye fitting 36 may be provided as shown to couple the patient interface 28 to the inspiratory limb 32 and the expiratory limb 34 of the circuit 30.

The present description contemplates that the patient interface 28 may be invasive or non-invasive, and of any configuration suitable for establishing a flow of breathing gas from the patient circuit 30 to an airway of the patient 24. Examples of suitable patient interface 28 devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. The inspiratory limb 32 receives a gas mixture from one or more gas sources controlled by one or more gas metering devices. The pneumatic system 22 may include a variety of other components, including other sources for pressurized air and/or oxygen, gas metering devices, accumulators, mixing modules, valves, sensors, tubing, filters, etc.

Controller 50 is operatively coupled with pneumatic system 22, signal measurement and acquisition systems, and an operator interface 52. The operator interface 52 may be provided to enable an operator to interact with the ventilator 20 (e.g., change ventilator settings, select operational modes, view monitored parameters, etc.). Controller 50 may include memory 54, one or more processors 56, storage 58, and/or other components of the type commonly found in command and control computing devices.

The memory 54 is non-transitory computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of non-transitory computer-readable media contained herein refers to a solid-state storage, it should be appreciated by those skilled in the art that non-transitory computer-readable storage media can be any available media that can be accessed by the processor 56. Non-transitory computer-readable storage media includes volatile and non-volatile, removable and non-removable media implemented in any method or technology for storage of information such as computer-readable instructions, data structures, program modules or other data. Non-transitory computer-readable storage media includes, but is not limited to, RAM, ROM, EPROM, EEPROM, flash memory, non-volatile memory, or other solid state memory technology, CD-ROM, DVD, or other optical storage, magnetic cassettes, magnetic tape, magnetic disk storage or other magnetic storage devices, or any other medium which can be used to store the desired information and which can be accessed by the processor 56.

The controller 50 issues commands to pneumatic system 22 in order to control the gas delivery provided to the patient 24 by the ventilator 20. The specific commands may be based on inputs received from patient 24, pneumatic system 22 and sensors, operator interface 52 and/or other components of the ventilator 20.

In the depicted example, operator interface 52 includes a primary display 59 that is touch-sensitive, enabling the primary display 59 to serve both as an input user interface and an output device. The primary display 59 is removable from the ventilator system 20. The removal of primary display 59 provides for easy transport of the ventilator 20 (as primary displays are often large and consume high amounts of power) without interrupting the delivery of respiratory therapy to a patient. The primary display 59 can display any type of ventilation information, such as sensor readings, parameters, commands, alarms, warnings, and smart prompts (i.e., ventilator determined operator suggestions).

The primary display 59 is an electronic Graphical User Interface (GUI) that allows the operator to view patient data in different forms, view historical data, control the operation of the ventilator, and to change the therapy being provided to the patient. In an embodiment, every ventilator operation that can be performed by the ventilator 20 can be accessed via the electronic GUI 59. In another embodiment, a portion of the ventilator operations that can be performed by the ventilator 20 can be accessed via the electronic GUI of primary display 59.

In one embodiment, primary display 59 utilizes a separate GUI controller (not shown), which may alternatively be referred to as the primary display controller or graphics subsystem. A separate GUI controller may be utilized because the computing power necessary to drive primary display 59 is often solely dedicated to running the primary display, interpreting user inputs received through the GUI, and passing that information on to the main ventilator controller that controls the actual gas delivery operations of the ventilator and any subsystems within the ventilator.

Primary display 59 also performs the computations and manipulations necessary to convert raw data, provided by the main ventilator controller or discreet ventilator subsystems, into the graphical presentations, such as waveforms, loops, monitored patient data, and/or average values for display on the GUI. This list is not limiting. Any suitable type of graphical presentation for a primary display 59 may be utilized. In one embodiment, the raw data and the generated graphical presentations are stored in memory to be accessed as needed by the GUI controller of primary display 59.

In this embodiment, ventilator 20 includes a battery control system. Medical ventilators may be provided with one or more batteries to allow the ventilator to remain in operation without interruption while a patient is being transported between locations or during power loss. In this embodiment, the ventilator 20 monitors the charge state and performance of the battery or batteries and keeps the batteries in a charged state. In this embodiment, the primary display 59 and/or SSD 51 is in communication with the battery control system and displays battery information received from the battery control system, such as battery use, battery performance, and battery charge levels.

In an alternative embodiment, the primary display includes a primary display battery control system that monitors the charge state and performance of the battery or batteries in the ventilator system and/or in the primary display and keeps the batteries in a charged state. In this embodiment, the primary display 59 and/or SSD 51 is in communication with the primary display battery control system and displays battery information received from the battery control system, such as battery use, battery performance, and battery charge levels.

Ventilator 20 further includes system status display (SSD) 51. The SSD 51 is a secondary display that provides limited status information to the operator. As shown in FIG. 1, SSD 51 is not interactive in any way. SSD 51 displays status information in a predetermined or preselected format. In alternative embodiments, the SSD 51 provides for limited interactions, such as a set of commands provided directly to the controller 50.

SSD 51 is completely independent of the GUI controller on the primary display 59. Accordingly, if the primary display 59 with the GUI controller fails, is disconnected, removed from the ventilator 20, powered off, or malfunctions, the SSD 51 still provides the operator with ventilator and patient information obtained directly from the controller 50. SSD 51 allows an operator to determine the status of various subsystems of ventilator 20 without having to power up/boot up, fix, or reattach primary display 59 with the GUI controller.

In one embodiment, SSD 51 is located on the housing of ventilator 20. In an embodiment, SSD 51 displays status information and is always on when the ventilator is provided with battery power and/or external power (e.g., when it is plugged into a wall socket). In this embodiment, the SSD 51 is a small, low-power display, such as an LCD display. In an alternative embodiment, SSD 51 is powered off unless an operator turns the SSD 51 on (with different power switch from that controlling the primary display 59) when the ventilator is provided with battery power and/or external power. In another embodiment, SSD 51 has drive circuitry to determine when the primary display is turned off, disabled, failing or removed from the ventilator (e.g., such as for transport to conserve battery life) and automatically turns on for a portion of time. In this embodiment, SSD 51 may remain on. In another embodiment, SSD 51 remains on until the operator switches SSD 51 off, SSD 51 looses power, the primary display 59 is turned on, is fixed, or is reattached, or an external power source is utilized.

In one embodiment, SSD 51 is programmable by the operator or manufacturer to meet local requirements or preferences. Further, status data (that is obtained from systems other than the GUI controller of the primary display 59) is displayed. In another embodiment, the format of the data displayed on the SSD 51 is selected by the operator or manufacturer.

Figure 2:
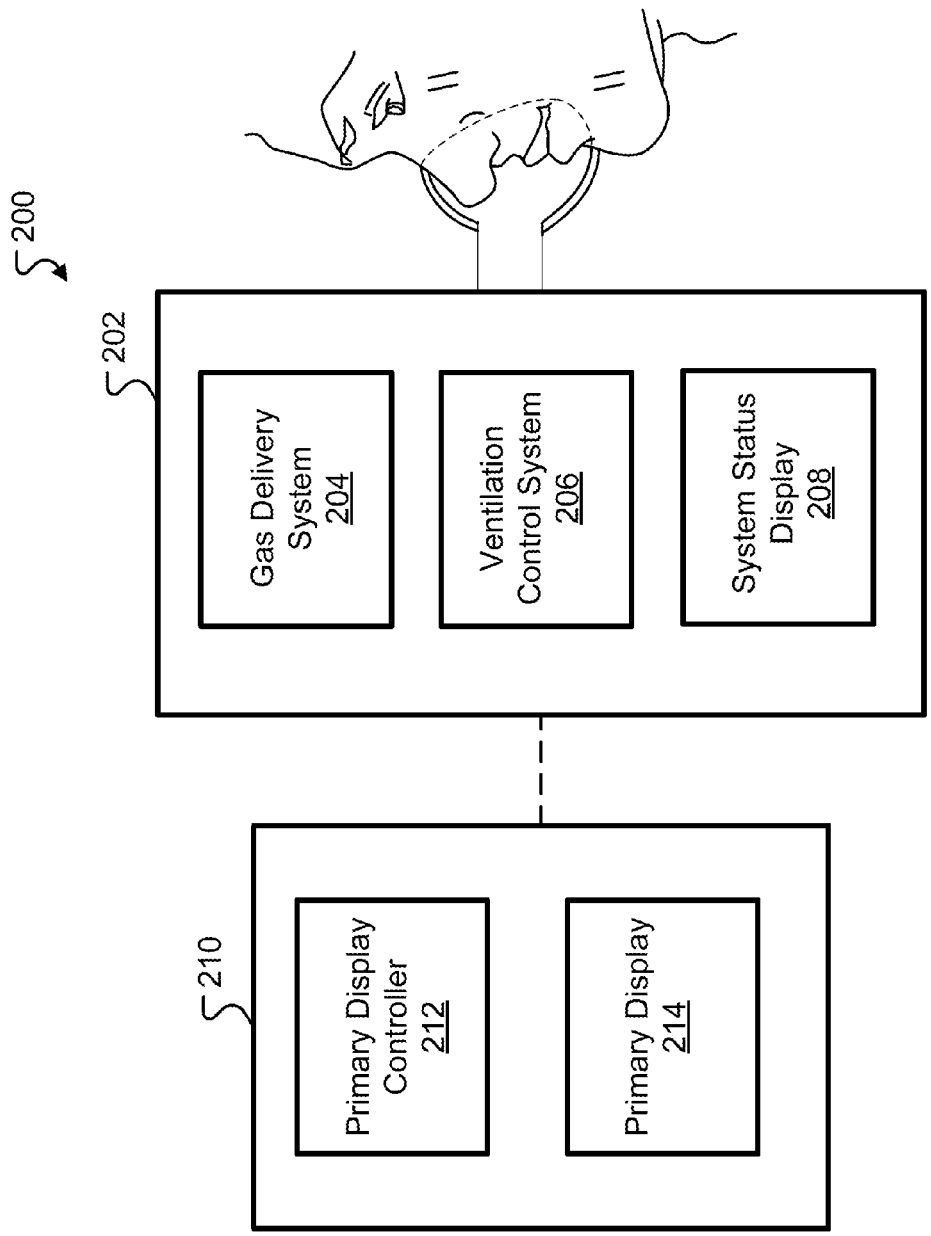
FIG. 2 illustrates an embodiment of a ventilator system including a primary removable display and a system status display.

Referring to FIG. 2, an embodiment of a ventilation system 200 is shown. Ventilation system 200 includes a main housing 202. The main housing includes a gas delivery system 204, a ventilation control system 206, and a system status display 208. The ventilation control system 206 controls the gas delivery system and monitors one or more of a patient physiological parameter, operational parameters of the ventilation system and user-settable parameters. In one embodiment, the ventilation control system 206 is located in the main housing 202. In an alternative embodiment, the ventilation control system 206 is located in a separate component independent of the main housing.

The system status display 208 receives status data directly from the ventilation control system and displays the status data. In one embodiment, the system status display 208 includes a switch that turns the system status display on and off. In another embodiment, at least one command is transmitted to the ventilation control system 206 via the system status display 208. In another embodiment, the at least one command is transmitted to the ventilation control system 206 via the system status display 208 upon user command. In one embodiment, the SSD commands include power save, primary display shut-down, system status display shut-down, stand-by, charge, breath-type set-up, pressure support set-up, oxygen percent set-up, tidal volume set-up, breath-type change, pressure support change, oxygen percent change, and/or tidal volume change. All of the commands listed above are not limiting. Other suitable commands for controlling a ventilator system may be added to the system status display.

The status data of the system status display 208 may display any suitable information, such as patient parameters, ventilation parameters, sensor readings, ventilator information, and/or calculated parameters. In one embodiment, the status data of the system status display 208 are selected from ventilator status, primary display status, the available gas sources, the utilized gas source or sources, the available power sources, the utilized power source, the pressure trace of inspiratory pressure or manometer, low pressure level (e.g., low positive end expiratory pressure or PEEP), peak inspiratory pressure ($P_{PEAK}$), battery system status, use of a battery, battery charge level, and battery status. All of this information may be depicted in any suitable manner utilizing icons, graphs, charts, text, light, light intensity, and/or color.

Figure 4:
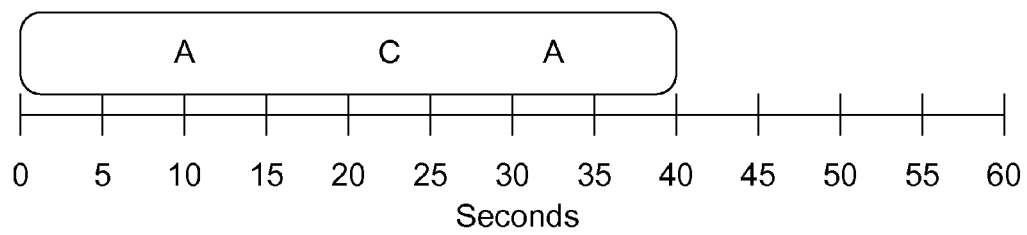
FIG. 4 illustrates an embodiment of a screen shot of a system status display.

In one embodiment, ventilator status includes ventilating status (i.e. actively ventilating a patient or not in use), primary display status, breath-type, warnings or alarms issued, and/or normal status (i.e. no warnings or alarms are being displayed or executed). In another embodiment, primary display status indicates at least one of whether the primary display is attached to the ventilator, displaying the graphical user interface, or is in communication with the ventilator. In another embodiment, the breath type (Assist, Control, & Spontaneous) utilized may be graphically display verses time, as illustrated in FIG. 4.

In yet another embodiment, battery system status includes if a battery is connected to the ventilator, if a battery is disconnected from the ventilator, if a battery is in use, if a battery is charged, charge level of a battery and/or an estimate of battery life. The charge level of the battery may be depicted as a fuel gauge or as a time duration counting down the amount of useable life left on the battery.

Figure 3:
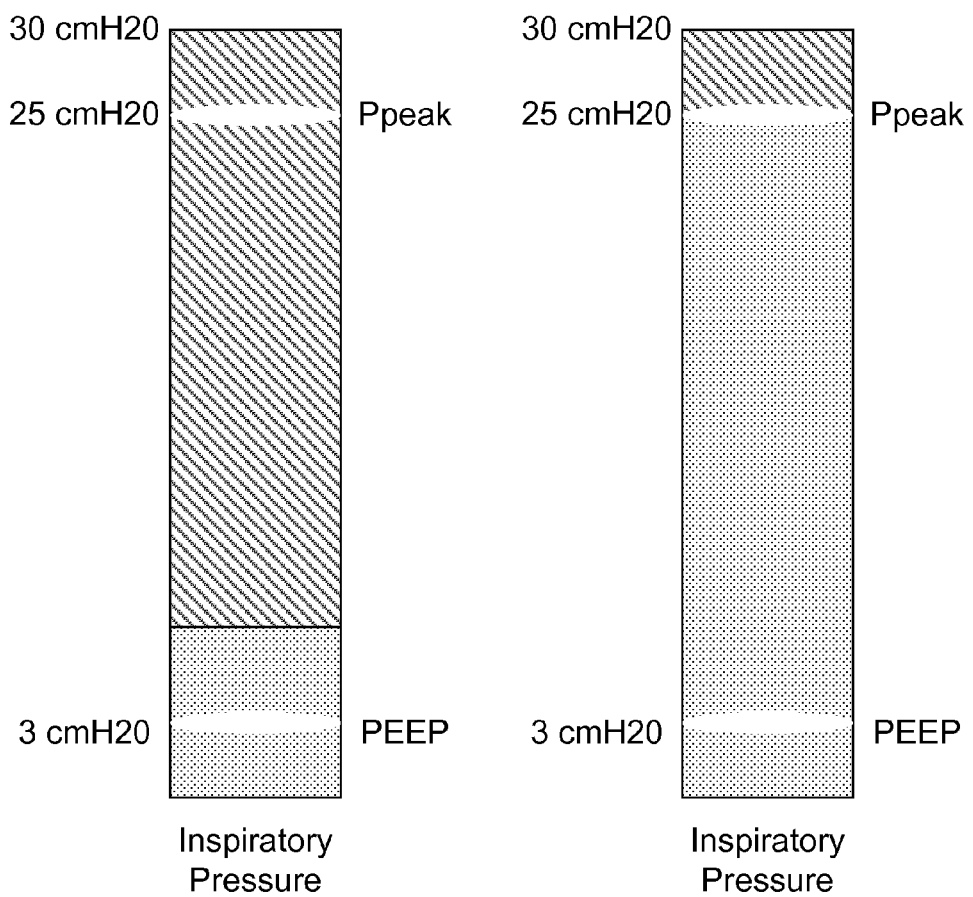
FIG. 3 illustrates an embodiment of a screen shot of a system status display.

The manometer may display the peak inspiratory pressure ($P_{PEAK}$), PEEP, and inspiratory pressure in thermometer-type display as illustrated in FIG. 3. As the inspiratory pressure changes, the manometer may demonstrate this with the movement of the pressure meter up and down the vertical scale. In a further embodiment, the manometer may illustrate high and low alarm setting for the peak inspiratory pressure. In another embodiment, the pressure ranges of the manometer may change based on the patient setting (e.g. adult, pediatric, or neonate) of the ventilator.

Ventilation system 200 further includes a primary display housing 210. The primary display housing 210 is removably attached to the main housing 202. In this embodiment, the primary display housing 210 includes a primary display controller 212 and a primary display 214, as illustrated in FIG. 2. In an alternative embodiment, the primary display controller 212 is located in the main housing 202. In another embodiment, the primary display controller 212 is located in a separate component independent of the main housing 202 and the primary display housing 210.

Primary display 214 presents the graphical user interface. In one embodiment, the primary display 214 includes a mechanism that turns the primary display 214 on and off. In another embodiment, the system status display 208, when in operation, uses at least less than 10%, more preferable less than 5% and even more preferably less than 2% of the power used by the primary display when in operation. In yet another embodiment, the system status display 208, when in operation, uses at least less than 50% of the power used by the primary display when in operation. In yet a further embodiment, the system status display 208, when in operation, uses at least less than 80% of the power used by the primary display 214 when in operation In an alternative embodiment, the system status display 208 has a low-power mode for conserving power consumption. The low-power mode reduced the amount of power consumed by the SSD 208 by at least 10%. In one embodiment, the low-power mode reduced the amount of power consumed by the SSD 208 by at least 50%. In another embodiment, the low-power mode reduced the amount of power consumed by the SSD 208 by at least 80%. In one embodiment, the SSD 208 enters the low-power mode when the primary display housing 210 is removed. In an additional embodiment, the SSD 208 is placed in a low-power mode when the primary display housing 210 is malfunctioning or disconnected. In another embodiment, the SSD 208 enters a low-power mode based on user command.

Primary display controller 212 generates the graphical user interface, receives user inputs through the graphical user interface, and delivers commands to the ventilation control system based on the inputs. In one embodiment, the primary display controller 212 places the primary display 214 in a safe disconnect mode to allow the primary display housing 210 to be removed. In an additional embodiment, the primary display controller 212 is placed in a low-power mode when the primary display housing 210 is removed. In another embodiment, the primary display controller 212 is turned off when the primary display housing 210 is removed. In yet another embodiment, the primary display controller 212 is turned off or placed in a low-power mode based on user command.

In one embodiment, the at least one command from the system status display 208 is transmitted to the ventilation control system 206 via a controller of system status display 208 when the primary display housing 210 is removed, turned off, disabled, and/or malfunctioning. In another embodiment, when the ventilation system 200 is ventilating a patient, the ventilation control system 206 causes the system status display 208 to display a first set of status data when the primary display housing 210 is attached and a second set of status data different from the first set of status data when the primary display housing 210 is removed.

In one embodiment, ventilation system 200 includes one or more batteries. In another embodiment, when the ventilation system 200 is ventilating a patient, the primary display controller 212 and primary display 214 are placed in a low-power mode when the ventilation system 200 is powered from the one or more batteries. In another embodiment, the primary display controller 212 and primary display 214 are placed in a low-power mode upon user command. In a further embodiment, when the ventilation system 200 is ventilating a patient, the primary display controller 212 and primary display 214 are turned off when the ventilation system 200 is powered from the one or more batteries. In an alternative embodiment, when the ventilation system 200 is ventilating a patient, the primary display controller 212 and primary display 214 are turned off based on user command. In an additional embodiment, when the ventilation system 200 is ventilating a patient, the ventilation control system 206 causes the system status display 208 to display a third set of status data when the ventilation system 200 is powered from an external source and a fourth set of status data different from the third set of status data when the ventilation system 200 is powered from the one or more batteries. In yet another embodiment, the ventilation control system 206 causes the system status display 208 to display a fifth set of status data when the ventilation system 200 is powered from an external source and the primary display 214 is turned off. In an alternative embodiment, the ventilation control system 206 causes the system status display 208 to display the first set of status data, the second set of status data, the third set of status data, the fourth set of status data, or the fifth set of status data based on user command.

Figure 10:
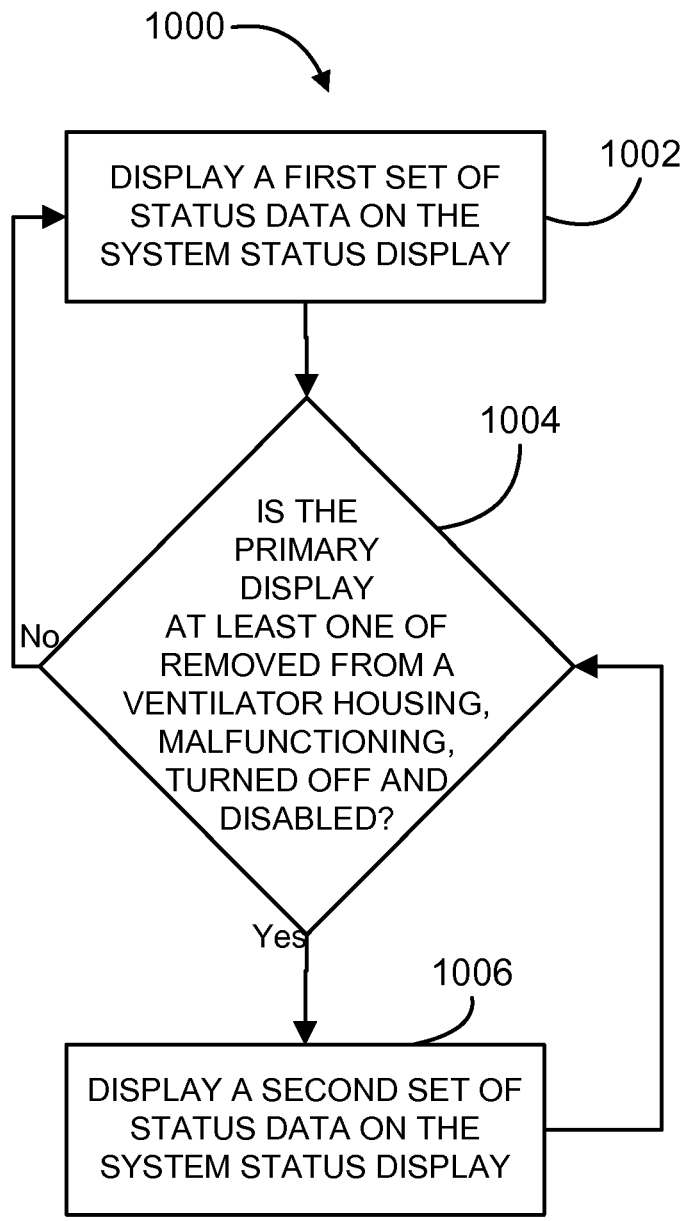
FIG. 10 illustrates an embodiment of a method for displaying ventilator information.

FIG. 10 illustrates a method for displaying ventilator information 1000. As illustrated, method 1000 displays a first set of status data on the system status display 1002. In one embodiment, the first set of status data is at least one of ventilator status, available gas sources, utilized gas source or sources, available power sources, utilized power source, pressure trace of inspiratory pressure, low pressure level (PEEP), peak inspiratory pressure, battery system status, batteries in use, battery charge level, and a battery status. In another embodiment, the first set of data displayed by first display operation 1002 is the screen shot of an SSD illustrated in FIG. 3. In yet another embodiment, the first set of data displayed by first display operation 1002 is the screen shot of an SSD illustrated in FIG. 4.

Next, method 1000 utilizes a determination operation 1004. Determination operation 1004 determines if the primary display is at least one of removed from a ventilator housing, malfunctioning, turned off, and disabled. If determination operation 1004 determines that the primary display is removed from a ventilator housing, malfunctioning, turned off, and/or disabled, determination operation 1004 selects to perform a second display operation 1006. If determination operation 1004 determines that the primary display is not removed from a ventilator housing, malfunctioning, turned off, and disabled, determination operation 1004 selects to perform first display operation 1002. In one embodiment, method 1000 removes the primary display from the main housing. In this embodiment, the determination operation 1004 determines that the primary display is removed from the primary housing and selects to perform a second display operation 1006.

The second display operation 1006 displays a second set of status data on the system status display that is different from the first set of status data. In one embodiment, the second set of status data is at least one of ventilator status, available gas sources, utilized gas source or sources, available power sources, utilized power source, pressure trace of inspiratory pressure, low pressure level (Peep), peak inspiratory pressure ($P_{PEAK}$), breath type (i.e. Assist, Control, or Spontaneous), battery system status, batteries in use, battery charge level, and a battery status. In one embodiment, the second set of status display data displayed by second display operation 1006 is the screen shot of an SSD illustrated in FIG. 7. In another embodiment, the second set of status display data displayed by the second display operation 1006 is the screen shot of an SSD illustrated in FIG. 8.

Figure 5:
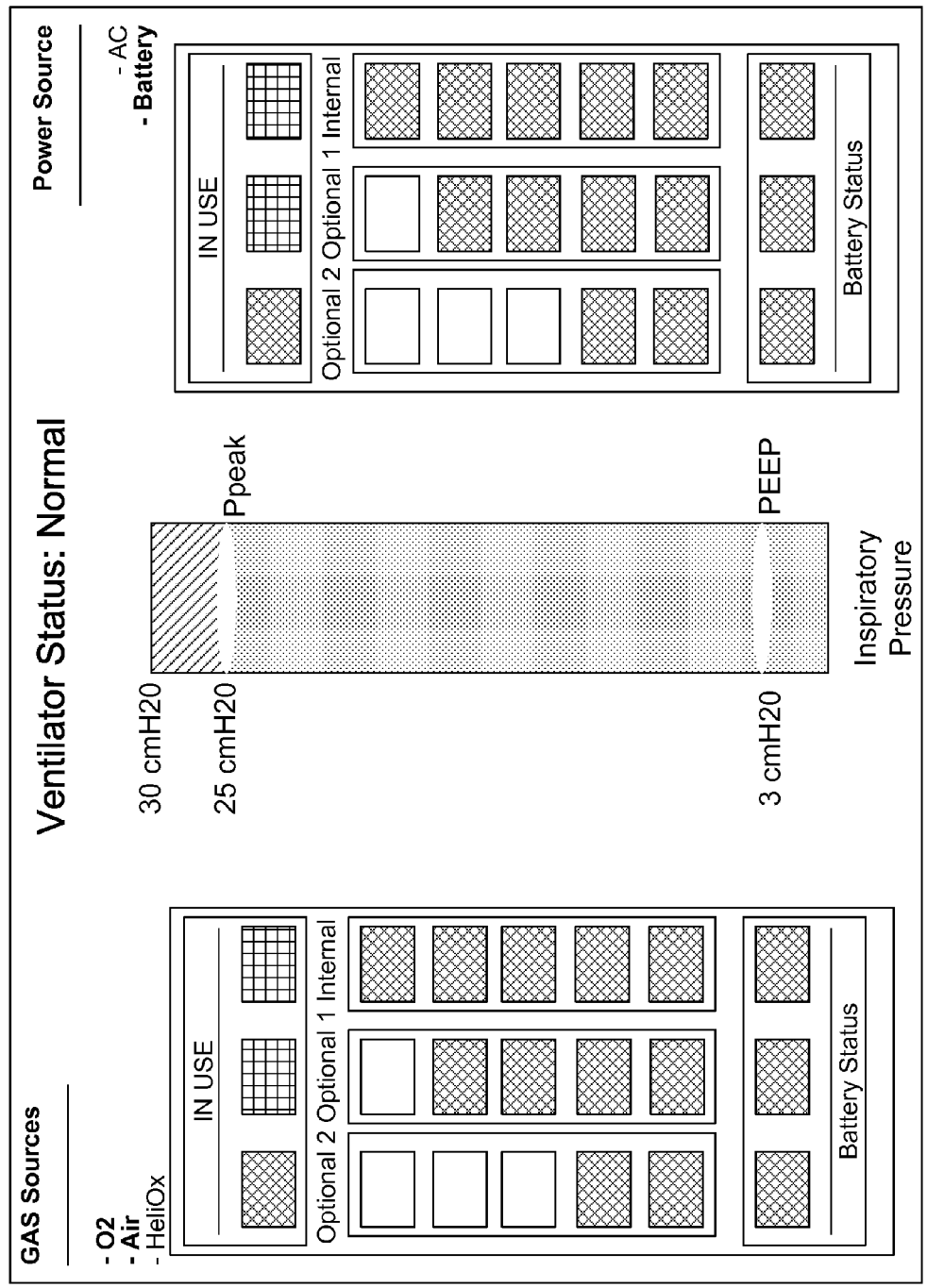
FIG. 5 illustrates an embodiment of a screen shot of a system status display.

In one embodiment, the second set of status display data displayed by a second display operation 1006 is the screen shot of an SSD illustrated in FIG. 5. In an additional embodiment, the second set of status display data displayed by second display operation 1006 is the screen shot of an SSD illustrated in FIG. 6.

After the performance of the second display operation 1006, method 1000 performs determination operation 1004 again. In one embodiment, method 1000 further includes utilizing less than 10% of power used by the primary display when in operation to power the system status display. In another embodiment, method 1000 further includes utilizing less than 50% of power used by the primary display when in operation to power the system status display. In yet another embodiment, method 1000 further includes utilizing less than 80% of power used by the primary display when in operation to power the system status display. Accordingly, the operation of the system status display utilizes less power than the operation of the primary display.

Figure 11:
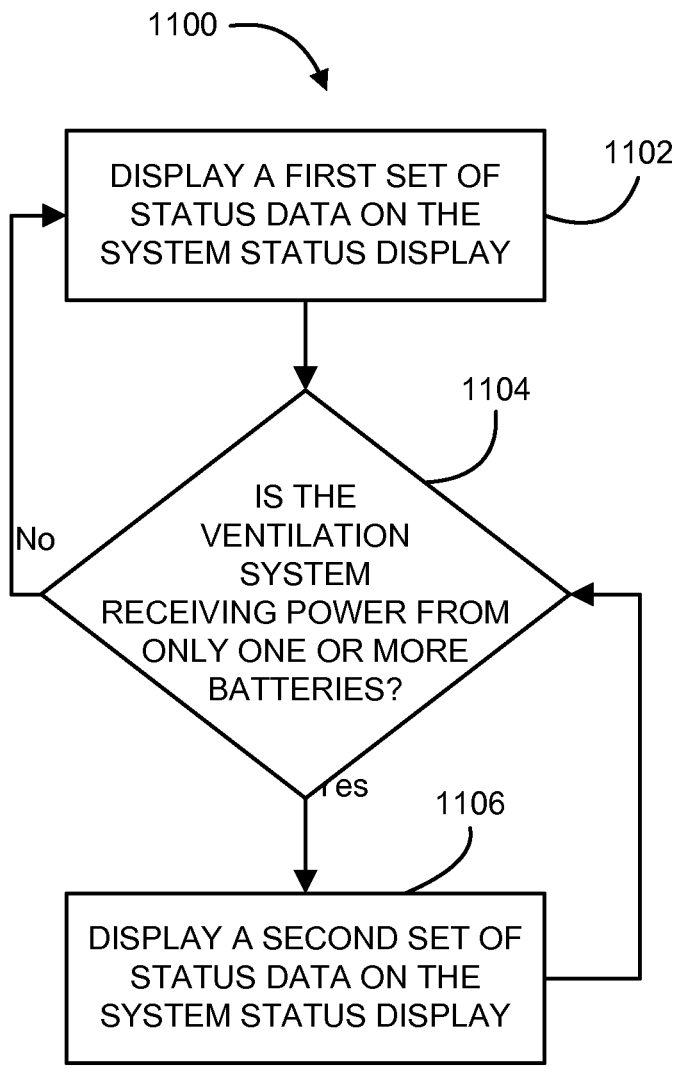
FIG. 11 illustrates an embodiment of a method for displaying ventilator information.

FIG. 11 illustrates a method for displaying ventilator information 1100. As illustrated, method 1100 displays a first set of status data on the system status display 1102. In one embodiment, the first set of status data is at least one of ventilator status, available gas sources, utilized gas source or sources, available power sources, utilized power source, pressure trace of inspiratory pressure, low pressure level (PEEP), peak inspiratory pressure, breath type (i.e. Assist, Control, or Spontaneous), battery system status, batteries in use, battery charge level, and a battery status. In another embodiment, the first set of data displayed by display operation 1102 is the screen shot of an SSD illustrated in FIG. 3. In a further embodiment, the first set of data displayed by display operation 1102 is the screen shot of an SSD illustrated in FIG. 4.

Next, method 1100 utilizes a determination operation 1104. Determination operation 1104 determines if a ventilation system is receiving power from only one or more batteries. If determination operation 1104 determines that the ventilation system is receiving power from only one or more batteries, determination operation 1104 selects to perform display operation 1106. If determination operation 1104 determines that the ventilation system is not receiving power from only one or more batteries, determination operation 1104 selects to perform the display operation 1102.

The display operation 1106 displays a second set of status data on the system status display that is different from the first set of status data. In one embodiment, the second set of status data is at least one of ventilator status, available gas sources, utilized gas source or sources, available power sources, utilized power source, pressure trace of inspiratory pressure, low pressure level (Peep), peak inspiratory pressure, breath type (i.e. Assist, Control, or Spontaneous), battery system status, batteries in use, battery charge level, and a battery status. In another embodiment, the second set of status display data displayed by display operation 1106 is the screen shot of an SSD illustrated in FIG. 5. In yet another embodiment, the second set of status display data displayed by display operation 1106 is the screen shot of an SSD illustrated in FIG. 6. In a further embodiment, the second set of status display data displayed by display operation 1106 is the screen shot of an SSD illustrated in FIG. 7. In an additional embodiment, the second set of status display data displayed by display operation 1106 is the screen shot of an SSD illustrated in FIG. 8.

After the performance of the display operation 1106, method 1100 performs determination operation 1104 again. In one embodiment, method 1100 further includes utilizing less than 50% of power used by the primary display when in operation to power the system status display when in operation. In another embodiment, method 1100 further includes utilizing less than 10% of power used by the primary display when in operation to power the system status display when in operation. In yet another embodiment, method 1100 further includes utilizing less than 80% of power used by the primary display when in operation to power the system status display when in operation. Accordingly, the operation of the system status display utilizes less power than the operation of the primary display and will allow the ventilation system to utilize less power when relying on battery power to operate.

In a further embodiment, method 1100 includes a primary display determination operation. In this embodiment, determination operation 1104 selects to perform the primary display determination operation if determination operation 1104 determines that the ventilation system is receiving power from only one or more batteries instead of selecting to perform display operation 1106. In this embodiment, the primary display determination operation determines if the primary display is at least one of removed from a ventilator main housing, malfunctioning, turned off, and disabled. If primary display determination operation determines that the primary display is removed from a ventilator housing, malfunctioning, turned off, and/or disabled, primary display determination operation selects to perform a third display operation. In this embodiment, the third display operation displays a third set of status data on the system status display that is different from the first set of status data and different from the second set of status data. After performing the third display operation, method 1100 performs the determination operation 1104 again. If primary display determination operation determines that the primary display is not removed from a ventilator housing, malfunctioning, turned off, and disabled, primary display determination operation selects to perform the display operation 1106.

Figure 12:
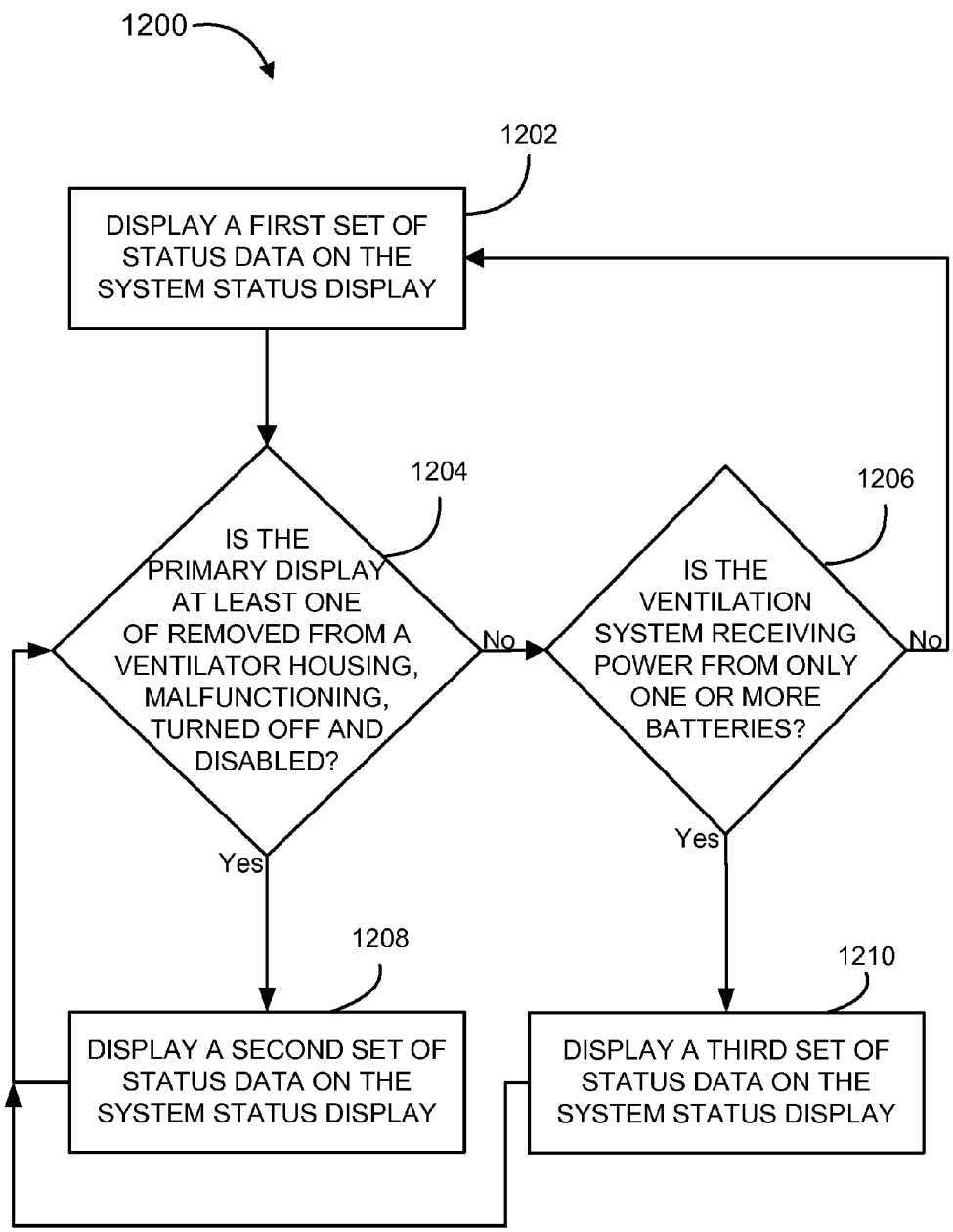
FIG. 12 illustrates an embodiment of a method for displaying ventilator information.

FIG. 12 illustrates a method for displaying ventilator information 1200. As illustrated, method 1200 displays a first set of status data on the system status display 1202. In one embodiment, the first set of status data is at least one of ventilator status, available gas sources, utilized gas source or sources, available power sources, utilized power source, pressure trace of inspiratory pressure, low pressure level (PEEP), peak inspiratory pressure ($P_{PEAK}$), breath type (i.e. Assist, Control, or Spontaneous), battery system status, batteries in use, battery charge level, and a battery status. In another embodiment, the first set of data displayed by display operation 1202 is the screen shot of an SSD illustrated in FIG. 3. In a further embodiment, the first set of data displayed by display operation 1202 is the screen shot of an SSD illustrated in FIG. 4.

Next, method 1200 utilizes a first determination operation 1204. First determination operation 1204 determines if the primary display is at least one of removed from a ventilator housing, malfunctioning, turned off, and disabled. If first determination operation 1204 determines that the primary display is removed from a ventilator housing, malfunctioning, turned off, and/or disabled, first determination operation 1204 selects to perform a second display operation 1208. If first determination operation 1204 determines that the primary display is not removed from a ventilator housing, malfunctioning, turned off, and disabled, first determination operation 1204 selects to perform a second determination operation 1206.

Second determination operation 1206 determines if a ventilation system is receiving power from only one or more batteries. If second determination operation 1206 determines that the ventilation system is receiving power from only one or more batteries, second determination operation 1206 selects to perform a third display operation 1210. If second determination operation 1206 determines that the ventilation system is not receiving power from only one or more batteries, second determination operation 1206 selects to perform the display operation 1202.

The second display operation 1208 displays a second set of status data on the system status display that is different from the first set of status data. In one embodiment, the second set of status data is at least one of ventilator status, available gas sources, utilized gas source or sources, available power sources, utilized power source, pressure trace of inspiratory pressure, low pressure level (Peep), peak inspiratory pressure, breath type (i.e. Assist, Control, or Spontaneous), battery system status, batteries in use, battery charge level, and a battery status. In another embodiment, the second set of status display data displayed by second display operation 1208 is the screen shot of an SSD illustrated in FIG. 5. In a further embodiment, the second set of status display data displayed by second display operation 1208 is the screen shot of an SSD illustrated in FIG. 7. In an additional embodiment, the second set of status display data displayed by second display operation 1208 is the screen shot of an SSD illustrated in FIG. 8. In one embodiment, the second set of status display data displayed by display operation 1208 is the screen shot of an SSD illustrated in FIG. 6.

The third display operation 1210 displays a third set of status data on the system status display that is different from the first set of status data. The second and third set of status data may be the same or different. In one embodiment, the third set of status data is at least one of ventilator status, available gas sources, utilized gas source or sources, available power sources, utilized power source, pressure trace of inspiratory pressure, low pressure level (Peep), peak inspiratory pressure, breath type (Assist, Control, or Spontaneous), battery system status, batteries in use, battery charge level, and a battery status. In another embodiment, the third set of status display data displayed by third display operation 1208 is the screen shot of an SSD illustrated in FIG. 5. In a further embodiment, the third set of status display data displayed by third display operation 1208 is the screen shot of an SSD illustrated in FIG. 7. In an additional embodiment, the third set of status display data displayed by third display operation 1208 is the screen shot of an SSD illustrated in FIG. 8.

In one embodiment, the order of the first determination step 1204 and second determination operation 1206 may be switched. In this embodiment, if second determination operation 1206 determines that the ventilation system is not receiving power from only one or more batteries, second determination operation 1206 selects to perform first determination operation 1204. Accordingly, in this embodiment, if first determination operation 1204 determines that the primary display is not removed from a ventilator housing, malfunctioning, turned off, and disabled, first determination operation 1204 selects to perform the display operation 1202.

After the performance of the second display operation 1208, method 1200 performs first determination operation 1204 again. In one embodiment, method 1200 includes utilizing less than 10% of power used by the primary display when in operation to power the system status display when in operation. In another embodiment, method 1200 includes utilizing less than 50% of power used by the primary display when in operation to power the system status display when in operation. In yet another embodiment, method 1200 includes utilizing less than 80% of power used by the primary display when in operation to power the system status display when in operation. Accordingly, the operation of the system status display utilizes less power than the operation of the primary display and will allow the ventilation system to utilize less power when relying on battery power to operate.

Figure 13:
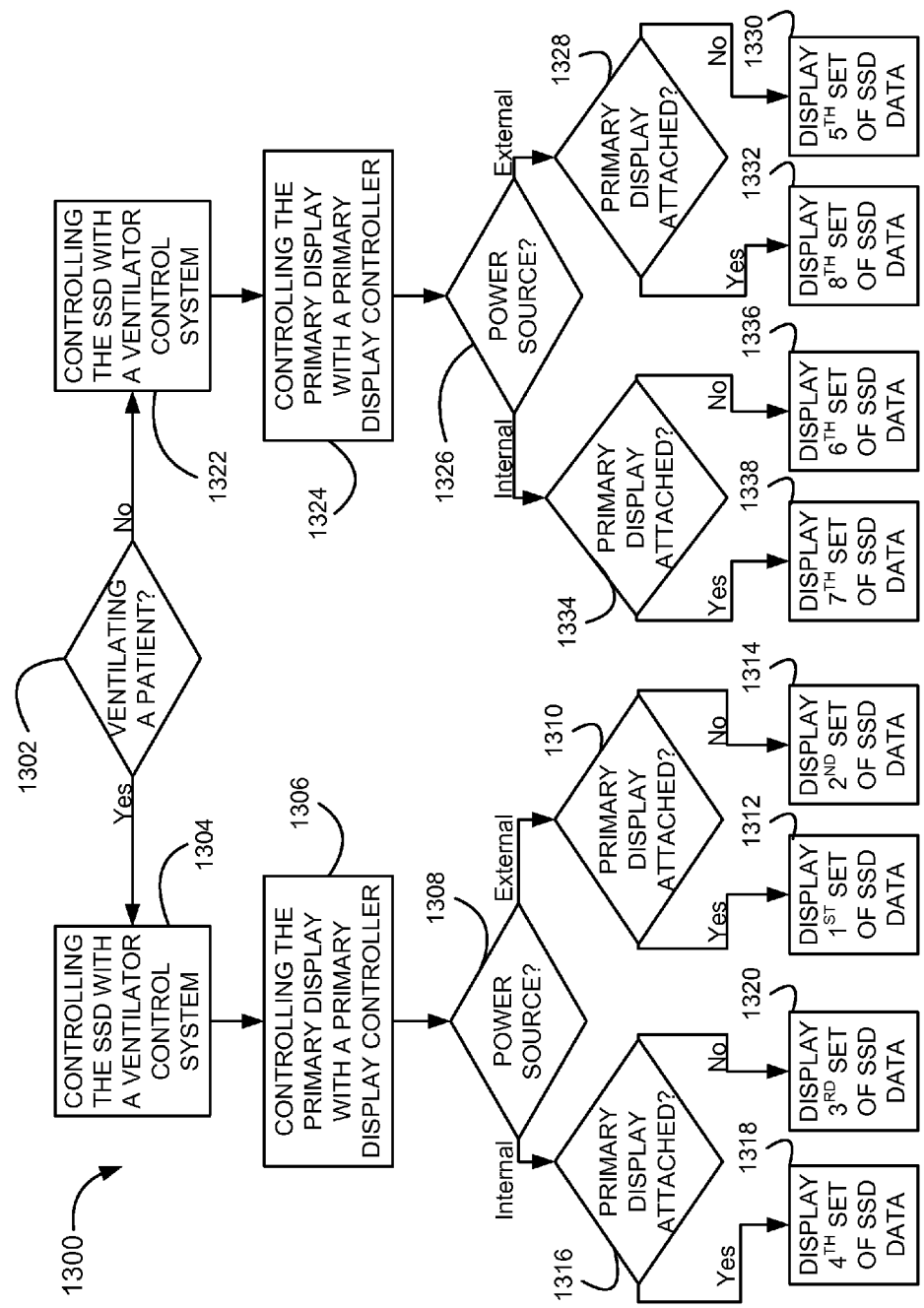
FIG. 13 illustrates an embodiment of a method for displaying ventilator information.

FIG. 13 illustrates a method for displaying ventilator information 1300. As illustrated, method 1300 determines if a ventilator system is ventilating a patient 1302. The ventilator system includes a primary display removable from a ventilator housing and a system status display (SSD). If determination operation 1302 determines that the ventilator system is ventilating a patient, determination operation 1302 selects to perform the SSD control operation 1304, the primary display control operation 1306, and determination operation 1308.

Control operation 1304 controls the SSD with a ventilator control system. Control operation 1306 controls the primary display with a primary display controller. Determination operation 1308 determines whether an internal power or an external power source is being utilized by the ventilator. If determination operation 1308 determines that the ventilator is utilizing an external power source, determination operation 1308 selects to perform determination operation 1310. If determination operation 1308 determines that the ventilator is utilizing an internal power source, determination operation 1308 selects to perform determination operation 1316.

Determination operations 1310 and 1316 determine if the primary display is attached to the main ventilator housing and if the primary display is displaying the graphical user interface. If determination operation 1310 determines that the primary display is attached to the main ventilator housing and that the primary display is displaying the graphical user interface, determination operation 1310 selects to perform display operation 1312. Display operation 1312 displays a first set of SSD data. If determination operation 1310 determines that the primary display is not attached to the main ventilator housing and that the primary display is not displaying the graphical user interface, determination operation 1310 selects to perform display operation 1314. Display operation 1314 displays a second set of SSD data.

If determination operation 1316 determines that the primary display is not attached to the main ventilator housing and that the primary display is not displaying the graphical user interface, determination operation 1316 selects to perform display operation 1320. Display operation 1320 displays a third set of SSD data. If determination operation 1316 determines that the primary display is attached to the main ventilator housing and that the primary display is displaying the graphical user interface, determination operation 1316 selects to perform display operation 1318. Display operation 1318 displays a fourth set of SSD data.

If determination operation 1302 of method 1300 determines that the ventilator system is not ventilating a patient, determination operation 1302 selects to perform the SSD control operation 1322, the primary display control operation 1324, and determination operation 1326.

Control operation 1322 controls the SSD with a ventilator control system. Control operation 1324 controls the primary display with a primary display controller. Determination operation 1326 determines whether an internal power or an external power source is being utilized by the ventilator. If determination operation 1326 determines that the ventilator is utilizing an external power source, determination operation 1326 selects to perform determination operation 1328. If determination operation 1326 determines that the ventilator is utilizing an internal power source, determination operation 1326 selects to perform determination operation 1334.

Determination operations 1328, 1334 determine if the primary display is attached to the main ventilator housing and if the primary display is displaying the graphical user interface. If determination operation 1328 determines that the primary display is attached to the main ventilator housing and that the primary display is displaying the graphical user interface, determination operation 1328 selects to perform display operation 1332. Display operation 1332 displays an eighth set of SSD data. If determination operation 1328 determines that the primary display is not attached to the main ventilator housing and that the primary display is not displaying the graphical user interface, determination operation 1328 selects to perform display operation 1330. Display operation 1330 displays a fifth set of SSD data.

If determination operation 1334 determines that the primary display is not attached to the main ventilator housing and that the primary display is not displaying the graphical user interface, determination operation 1334 selects to perform display operation 1336. Display operation 1336 displays a sixth set of SSD data. If determination operation 1334 determines that the primary display is attached to the main ventilator housing and that the primary display is displaying the graphical user interface, determination operation 1334 selects to perform display operation 1338. Display operation 1338 displays a seventh set of SSD data.

In one embodiment, method 1300 further includes operating the SSD on less power than the amount of power necessary to operate the primary display. In another embodiment, method 1300 utilizes less than 10% of power used by the primary display when in operation to power the system status display when in operation. In yet another embodiment, method 1300 utilizes less than 50% of power used by the primary display when in operation to power the system status display when in operation. In a further embodiment, method 1300 utilizes less than 80% of power used by the primary display when in operation to power the system status display when in operation.

In another embodiment, method 1300 displays a different set of data on the SSD based on at least one of a location of the primary display, data displayed on the primary display, and a power source. In one embodiment, the first, second, third, fourth, fifth, sixth, seventh, and eighth data sets are all different. In an alternative embodiment, at least one of the first, second, third, fourth, fifth, sixth, seventh, and eighth data sets are different. In another embodiment, the first, second, third, fourth, fifth, sixth, seventh, and eighth data sets are all the same. In a further embodiment, data and/or data sets displayed on the SSD is user selectable and/or configurable. In yet another embodiment, the data set displayed on the SSD is based on at least one of one of a location of the primary display, data displayed on the primary display, and a power source are user selectable and/or configurable.

In one embodiment, method 1300 displays at least one of sensor readings, ventilator parameters, ventilator calculations, and patient parameters on the SSD. In another embodiment, method 1300 displays at least one of ventilator status, available gas sources, utilized gas source or sources, available power sources, utilized power source, pressure trace of inspiratory pressure, low pressure level (Peep), peak inspiratory pressure, breath type (Assist, Control, or Spontaneous), battery system status, batteries in use, battery charge level, and a battery status. In one embodiment, the eighth set of SSD data and/or the fifth set of SSD data includes batteries in use, battery charge level, and/or a battery status.

Figure 14:
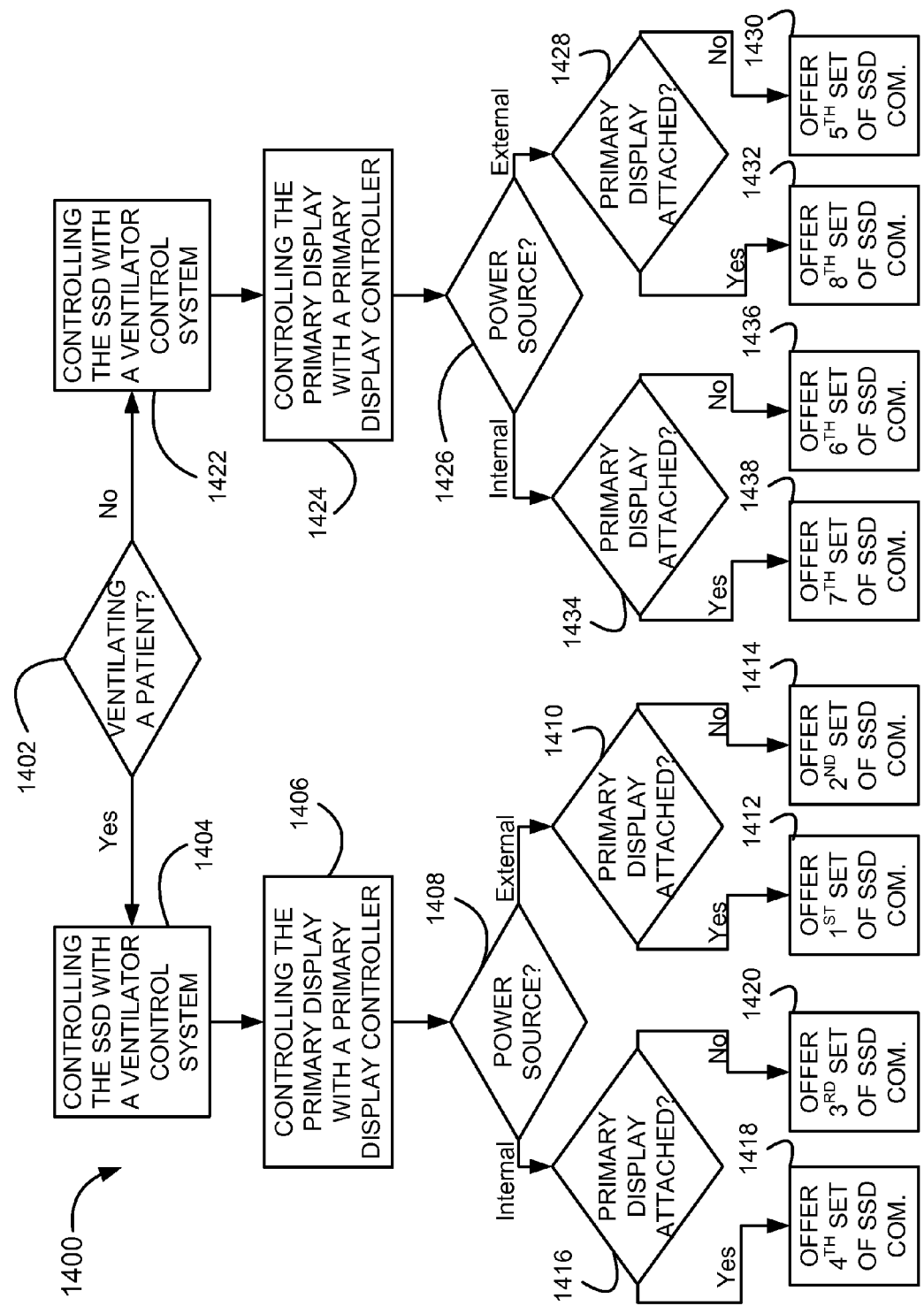
FIG. 14 illustrates an embodiment of a method for controlling a ventilator system.

FIG. 14 illustrates a method for controlling a ventilator system 1400. As illustrated, method 1400 determines if a ventilator system is ventilating a patient 1402. The ventilator system includes a primary display removable from a main ventilator housing and a system status display (SSD). If determination operation 1402 determines that the ventilator system is ventilating a patient, determination operation 1402 selects to perform the SSD control operation 1404, the primary display control operation 1406, and determination operation 1408.

Control operation 1404 controls the SSD with a ventilator control system. Further, the ventilation control system receives and executes user selected secondary commands from the system status display. Control operation 1406 controls the primary display with a primary display controller. Further, the primary display controller receives and executes user selected primary commands from the primary display. Determination operation 1408 determines whether an internal power or an external power source is being utilized by the ventilator. If determination operation 1408 determines that the ventilator is utilizing an external power source, determination operation 1408 selects to perform determination operation 1410. If determination operation 1408 determines that the ventilator is utilizing an internal power source, determination operation 1408 selects to perform determination operation 1416.

Determination operations 1410, 1416 determine if the primary display is attached to the main ventilator housing and if the primary display is displaying the graphical user interface. If determination operation 1410 determines that the primary display is attached to the main ventilator housing and that the primary display is displaying the graphical user interface, determination operation 1410 selects to offer a first set of SSD commands 1412. In one embodiment, the first set of SSD commands includes power save, primary display shut-down, system status display shut-down, breath-type change, pressure support change, oxygen percent change, and/or tidal volume change. In another embodiment, determination operation 1410 selects to offer no SSD secondary commands. If determination operation 1410 determines that the primary display is not attached to the main ventilator housing and that the primary display is not displaying the graphical user interface, determination operation 1410 selects to offer a second set of SSD commands 1414. In one embodiment, the second set of SSD commands includes power save, primary display shut-down, breath-type change, pressure support change, oxygen percent change, and/or tidal volume change.

If determination operation 1416 determines that the primary display is not attached to the main ventilator housing and that the primary display is not displaying the graphical user interface, determination operation 1416 selects to offer a third set of SSD commands 1420. In one embodiment, the third set of SSD commands includes power save, primary display shut-down, breath-type change, pressure support change, oxygen percent change, and/or tidal volume change.

If determination operation 1416 determines that the primary display is attached to the main ventilator housing and that the primary display is displaying the graphical user interface, determination operation 1416 selects to offer a fourth set of SSD commands 1418. In one embodiment, the fourth set of SSD commands includes power save, primary display shut-down, system status display shut-down, breath-type change, pressure support change, oxygen percent change, and/or tidal volume change.

If determination operation 1402 of method 1400 determines that the ventilator system is not ventilating a patient, determination operation 1402 selects to perform the SSD control operation 1422, the primary display control operation 1424, and determination operation 1426.

Control operation 1422 controls the SSD with a ventilator control system. Further, the ventilation control system receives and executes user selected secondary commands from the system status display. Control operation 1424 controls the primary display with a primary display controller. Further, the primary display controller receives and executes user selected primary commands from the primary display. Determination operation 1426 determines whether an internal power or an external power source is being utilized by the ventilator. If determination operation 1426 determines that the ventilator is utilizing an external power source, determination operation 1426 selects to perform determination operation 1428. If determination operation 1426 determines that the ventilator is utilizing an internal power source, determination operation 1426 selects to perform determination operation 1434.

Determination operations 1428, 1434 determine if the primary display is attached to the main ventilator housing and if the primary display is displaying the graphical user interface. If determination operation 1428 determines that the primary display is attached to the main ventilator housing and that the primary display is displaying the graphical user interface, determination operation 1428 selects to offer an eighth set of SSD commands 1432. In one embodiment, the eighth set of SSD commands includes power save, primary display shut-down, system status display shut-down, breath-type set-up, pressure support set-up, oxygen percent set-up, and/or tidal volume set-up.

If determination operation 1432 determines that the primary display is not attached to the main ventilator housing and that the primary display is not displaying the graphical user interface, determination operation 1432 selects to offer a fifth set of SSD commands 1430. In one embodiment, the first set of SSD commands includes power save, primary display shut-down, system status display shut-down, breath-type set-up, pressure support set-up, oxygen percent set-up, and/or tidal volume set-up.

If determination operation 1434 determines that the primary display is not attached to the main ventilator housing and that the primary display is not displaying the graphical user interface, determination operation 1434 selects to offer a sixth set of SSD commands 1436. In one embodiment, the sixth set of SSD commands includes power save, primary display shut-down, system status display shut-down, breath-type set-up, pressure support set-up, oxygen percent set-up, and/or tidal volume set-up. If determination operation 1434 determines that the primary display is attached to the main ventilator housing and that the primary display is displaying the graphical user interface, determination operation 1434 selects to offer a seventh set of SSD commands 1438. In one embodiment, the seventh set of SSD commands includes power save, primary display shut-down, system status display shut-down, breath-type set-up, pressure support set-up, oxygen percent set-up, and/or tidal volume set-up. All of the commands listed above for each feature are not limiting. Other suitable commands for controlling a ventilator system may be added to the system status display.

In one embodiment, method 1400 further includes operating the SSD on less power than the amount of power necessary to operate the primary display. In another embodiment, method 1400 utilizes less than 10% of power used by the primary display when in operation to power the system status display when in operation.

In another embodiment, method 1400 displays a different set of SSD commands on the SSD based on at least one of a location of the primary display, data displayed on the primary display, and a power source. In one embodiment, the first, second, third, fourth, fifth, sixth, seventh, and eighth sets of SSD commands are all different. In an alternative embodiment, at least one of the first, second, third, fourth, fifth, sixth, seventh, and eighth sets of SSD commands are different. In another embodiment, the first, second, third, fourth, fifth, sixth, seventh, and eighth sets of SSD commands are all the same. In a further embodiment, the commands displayed on the SSD are user selectable and/or configurable. In yet another embodiment, the set of commands on the SSD are based on at least one of one of a location of the primary display, data displayed on the primary display, and a power source are user selectable and/or configurable.

In one embodiment, method 1400 displays at least one of sensor readings, ventilator parameters, ventilator calculations, and patient parameters on the SSD. In another embodiment, method 1400 displays at least one of ventilator status, available gas sources, utilized gas source or sources, available power sources, utilized power source, pressure trace of inspiratory pressure, low pressure level (Peep), peak inspiratory pressure, battery system status, batteries in use, battery charge level, and a battery status.

In another embodiment, determination operations 1410, 1416, 1428, and 1434 may select to offer no secondary commands on the system status display. In a further embodiment, the user may select to not offer any secondary commands on the system status display.

It will be clear that the systems and methods described herein are well adapted to attain the ends and advantages mentioned as well as those inherent therein. Those skilled in the art will recognize that the methods and systems within this specification may be implemented in many manners and, as such, are not to be limited by the foregoing exemplified embodiments and examples. For example, the operations and steps of the embodiments of methods described herein may be combined or the sequence of the operations may be changed while still achieving the goals of the technology. In addition, specific functions and/or actions may also be allocated in such a way as to be performed by a different module or method step without deviating from the overall disclosure. In other words, functional elements being performed by a single or multiple components, in various combinations of hardware, firmware, and software, and individual functions can be distributed among software applications. In this regard, any number of the features of the different embodiments described herein may be combined into one single embodiment and alternate embodiments having fewer than or more than all of the features described herein are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

Unless otherwise indicated, all numbers expressing quantities, properties, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

EXAMPLES

The following are embodiments of displays that could be shown on the SSD of a medical ventilator.

The following are embodiments of pressure traces or manometer that could be displayed on SSD to allow an operator to determine from the SSD the ventilator's ability to support breath delivery to the patient.

In one embodiment, as the SSD displays a pressure trace or manometer that indicates that pressure is transitioning between two points, such as PEEP and Peak Inspiratory Pressure ($P_{PEAK}$). As illustrated in FIG. 3, an embodiment of a screen shot of an SSD, the SSD displays a pressure trace that provides an indication of the rise time of the pressure and the pressure levels. Further, as shown in the FIG. 3 embodiment, the SSD provides a continuous display of the minimum and peak inspiratory pressure levels. In one embodiment, the pressure trace can be scaled to provide for the highest level of resolution on the SSD.

While not shown in this embodiment, in an alternative embodiment, the manometer includes high and low peak inspiratory pressure alarms. The alarms can be shown as a mark graphically on the manometer or just listed as text beside the manometer. Additionally, while not shown in this embodiment, the ranges of the manometer change based on the selected patient setting. Accordingly, the pressure ranges vary depending upon if the ventilator is in an adult, pediatric, or neonate setting.

In another embodiment, the SSD displays current breath-type to allow an operator to determine from the SSD the ventilator's ability to support breath delivery to the patient. In one embodiment the SSD displays a breath-type indicator or shows the type of breath being delivered by the ventilator (Assist, Control, or Spontaneous). As illustrated in the embodiment of an SSD screen shot in FIG. 4, the SSD displays a continuous graph to show the type of breath being delivered verses time in seconds (i.e. A=Assist, C=Control, and S=Spontaneous, but is not shown).

The following are embodiments of the types of information that could be presented on an SSD to allow an operator to determine from the SSD the ventilator's ability to support breath delivery to the patient.

In one embodiment, the SSD displays ventilator status information, GUI summary information for the primary display, available gas sources and installed gas input connections, power system information, and/or battery system status information. The ventilator status information indicates the current mode of the ventilator, such as Normal, Stand-by, Charge, Back-Up Ventilation, Safety Valve Open, or Ventilator Inoperative. The summary information for the GUI on the primary display may include displaying a loss of GUI communication and other errors associated with the primary display. The available gas sources and installed gas input connections displayed may include Air, Oxygen, HeliOx, and/or Nitrogen. While not illustrated in this embodiment, the display may show other types of gas sources. The Power System Information displayed may include the active power source, such as AC or Battery power sources. In another embodiment the battery system status information may include if and which batteries are in use, battery charge level, such as graphically depicting the level as a fuel gauge and/or battery status (i.e. normal). In another embodiment, the battery charge level may be shown by the amount of use time the batteries have left. In a further embodiment, the fuel gauge depiction of the battery charge level may be color coded for easy interpretation.

In one embodiment, the SSD displays transport-specific information (displayed during patient transport. The patient transport information may include vital patient data and data presented in waveforms. In one embodiment, the SSD includes an input mechanism for making setting changes, invoking functions, and/or silencing alarms.

In another embodiment, the SSD displays internationalization/localization support data. In one embodiment, the internationalization/localization support data includes labeling and display information to be in multiple languages or language selectable, use of alpha/numeric support to produce one base configuration for the SSD that can be updated with software support during manufacturing, installation, and/or during operation, and adding character sets for multiple languages to allow an operator to change all patient and system information during use or during the patient setup.

In another embodiment, the SSD has additional support modes. In one embodiment, the SSD utilizes a low-power display. Accordingly, only a small amount of power is necessary to ventilator information on the SSD. In another embodiment, the SSD is operated by the ventilator in standby power. Standby power is a mode where generally only the ventilator controller circuitry is powered. In yet another embodiment, the SSD provides for a charge mode. The charge mode may include charging batteries while the ventilator is supplied with AC power and the power switch is in the off position and/or on position. Further, the SSD, in another embodiment displays fuel gauges and/or power system status. In one embodiment, SSD displays the status of installed options.

As illustrated in FIG. 5, an embodiment of an SSD screen shot is shown. In this embodiment, the SSD displays the following: ventilator status as normal; the available gas sources as air, oxygen, and heliox; the utilized gas sources as oxygen and air; the available power sources as AC and battery; the power source being utilized as battery; the pressure trace of inspiratory pressure including highlighted low pressure level (Peep) and peak inspiratory pressure ($P_{PEAK}$); and battery system status including showing that batteries were in use for both breath delivery and compressor, battery charge level depicted graphically as a fuel gauge for both the breath delivery and compressor batteries, and a battery status as normal for both the breath delivery and compressor batteries.

Figure 6:
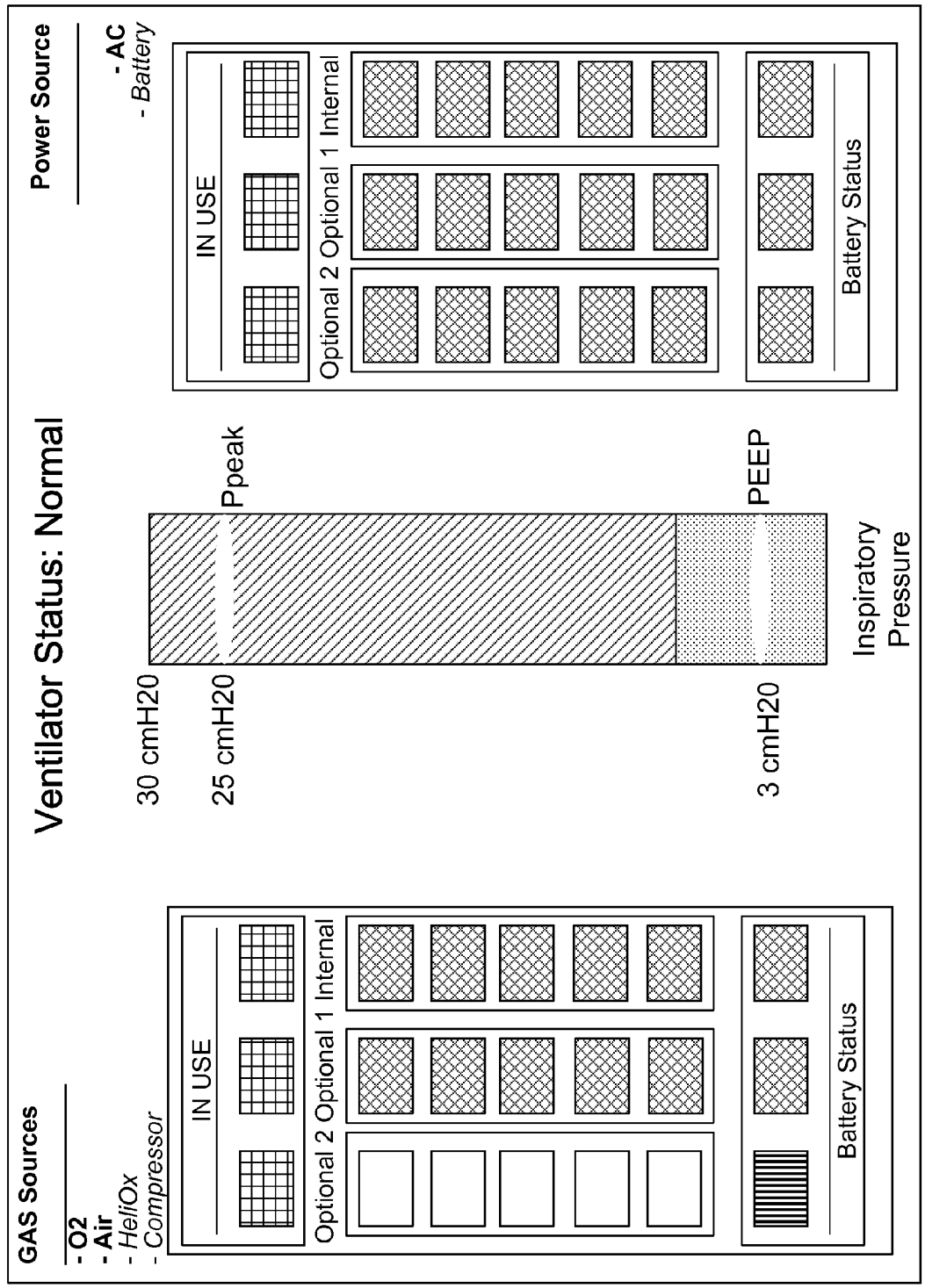
FIG. 6 illustrates an embodiment of a screen shot of a system status display.

As illustrated in FIG. 6, an embodiment of an SSD screen shot is shown. In this embodiment, the SSD displays the following: ventilator status as normal; the available gas sources as air, oxygen, and heliox; the utilized gas sources as oxygen and air; the available power sources as AC and battery; the power source being utilized as AC; the pressure trace of inspiratory pressure including highlighted low pressure level (Peep) and peak inspiratory pressure; and battery system status including depicting that neither the breath delivery or compressor were in use, the battery charge level graphically as a fuel gauge for both the breath delivery and compressor batteries, and a battery status as in default for the breath delivery battery and as normal for the compressor battery.

Figure 7:
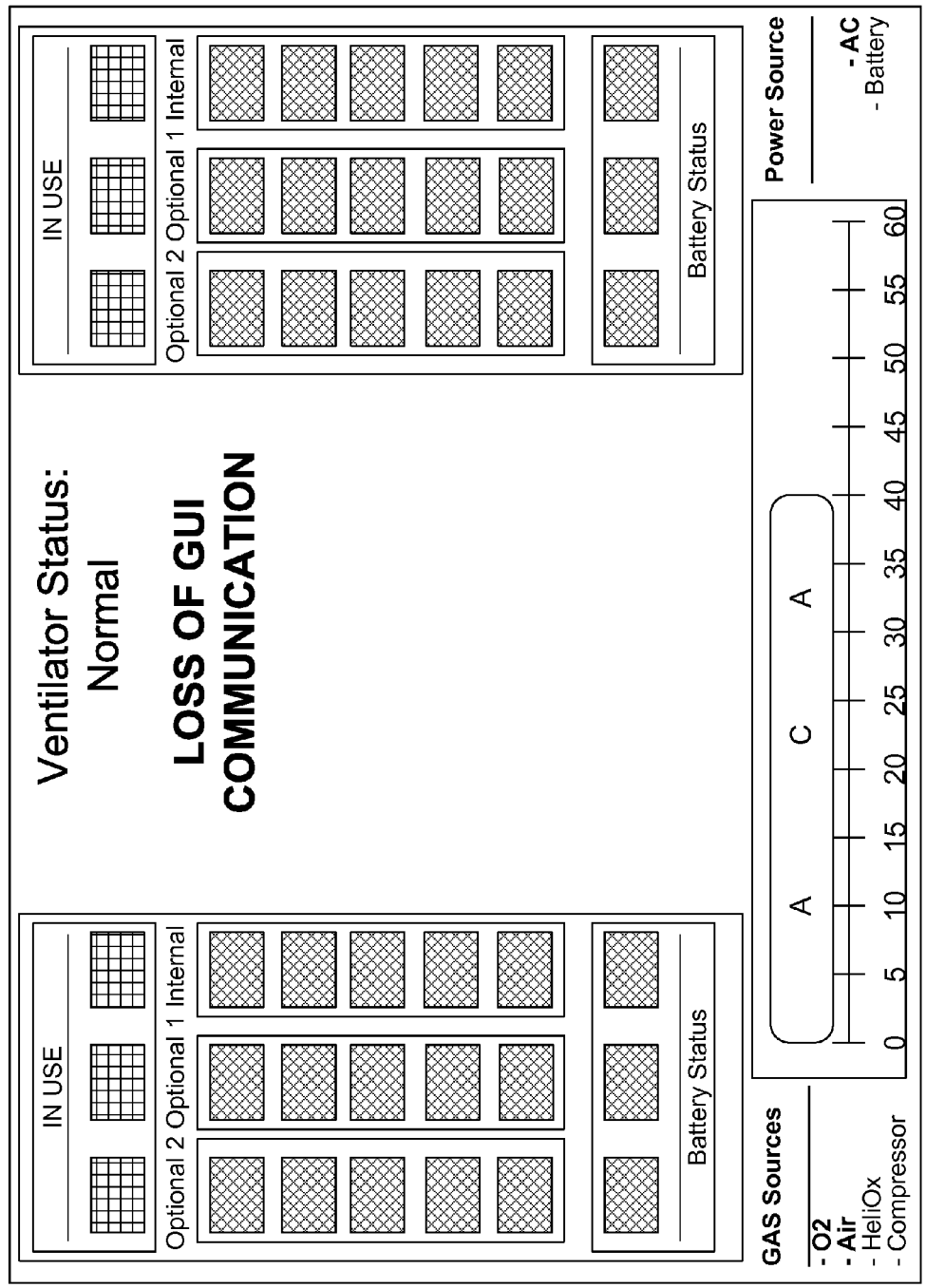
FIG. 7 illustrates an embodiment of a screen shot of a system status display.

As illustrated in FIG. 7, an embodiment of an SSD screen shot is shown. In this embodiment, the SSD displays the following: ventilator status as normal, with a loss of GUI communication; the available gas sources as air, oxygen, and heliox; the utilized gas sources as oxygen and air; the available power sources as AC and battery; the power source being utilized as AC; a breath-type indicator depicted graphically verses time in seconds; and a battery system status including depicting that neither the breath delivery or compressor were in use, the battery charge level graphically as a fuel gauge for both the breath delivery and compressor batteries, and a battery status as normal for both the breath delivery battery and the compressor battery.

Figure 8:
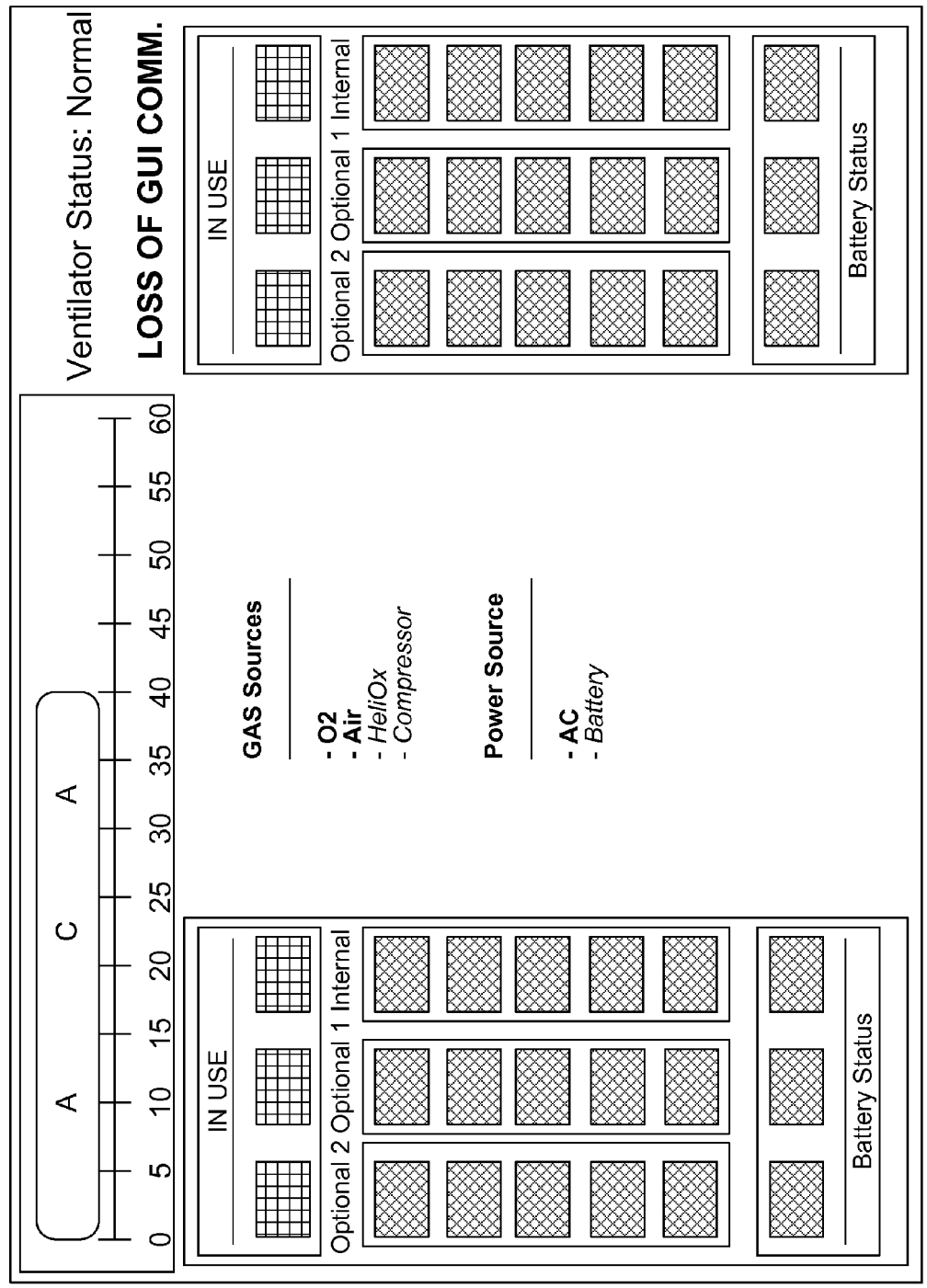
FIG. 8 illustrates an embodiment of a screen shot of a system status display.

As illustrated in FIG. 8, an embodiment of an SSD screen shot is shown. In this embodiment, the SSD displays the following: ventilator status as normal, with a loss of GUI communication; the available gas sources as air, oxygen, and heliox; the utilized gas sources as oxygen and air; the available power sources as AC and battery; the power source being utilized as AC; a breath-type indicator depicted graphically verses time in seconds; and a battery system status including depicting that neither the breath delivery or compressor were in use, the battery charge level graphically as a fuel gauge for both the breath delivery and compressor batteries, and a battery status as normal for both the breath delivery battery and the compressor battery. In this embodiment, as illustrated in FIG. 8, the breath-type indicator depicted graphically verses time in seconds is in a different location compared to FIG. 7.

Figure 9:
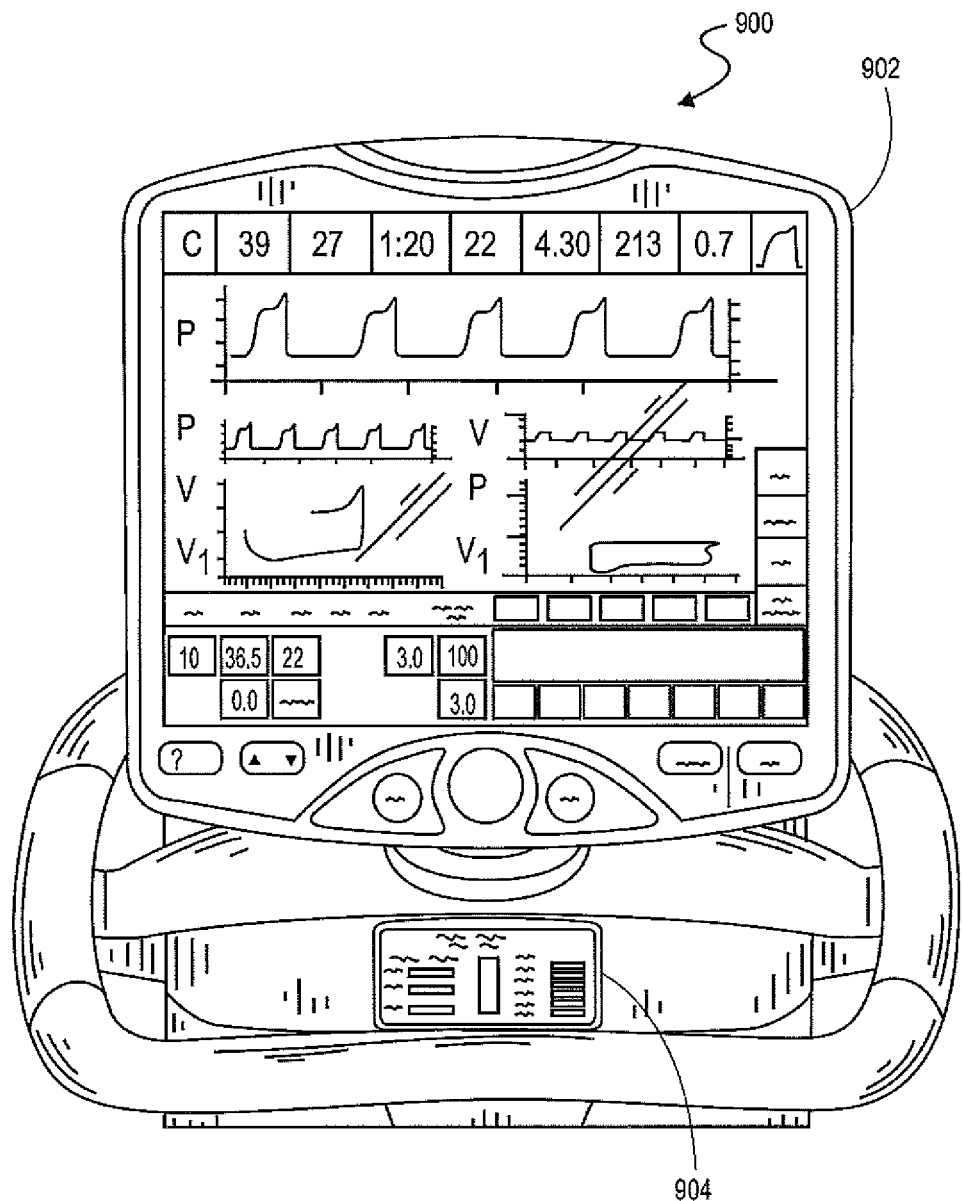
FIG. 9 illustrates an embodiment of a ventilator display system.

As illustrated in FIG. 9, an embodiment of a ventilator display system 900 is shown. The ventilator display system includes a primary removable display 902 and system status display (SSD) 904. In this embodiment, primary display 902 is an electronic GUI. The SSD 904 shown in FIG. 9 is a stand alone display, completely independent of the primary display and its related subsystems. Further, SSD 904 illustrates a redundant pressure trace (redundant in the sense that the same data is being display, albeit in a different format, on the primary display) that can be used to determine operational state of the breath delivery system. The redundant pressure trace displayed on SSD 904 is useful in the event of a primary display malfunction or as a transport device.

What is claimed is:

1. A ventilation system comprising:
   a main housing;
   a gas delivery system in the main housing;
   a ventilation control system in the main housing that controls the gas delivery system and monitors one or more of a patient physiological parameter, operational parameters of the ventilation system, and user-settable parameters;
   a primary display controller that generates a graphical user interface and that receives user inputs through the graphical user interface and capable of delivering primary commands to the ventilation control system based on the user inputs;
   a primary display housing removably attached to the main housing;
   a primary display in the primary display housing that presents the graphical user interface; and
   a system status display incorporated into the main housing that displays status data received from the ventilation control system and through which secondary commands may be input directly to the ventilation control system, wherein the secondary commands available for selection vary based at least on attachment of the primary display.

2. The ventilation system of claim 1 wherein:
   when the ventilation system is ventilating a patient and receiving power from an external power source and the primary display is attached to the main housing and is displaying the graphical user interface, no secondary commands are available for selection via the system status display.

3. The ventilation system of claim 1 wherein:
   when the ventilation system is ventilating a patient and is receiving power from an external power source and the primary display is attached to the main housing and is displaying the graphical user interface, one or more of the following secondary commands aremay be available for selection and received from the system status display and delivered to the ventilation control system:
   power save,
   primary display shut-down,
   system status display shut-down,
   breath-type change,
   pressure support change,
   oxygen percent change, and
   tidal volume change.

4. The ventilation system of claim 1 wherein:
   when the ventilation system is ventilating a patient and is receiving power from an external power source and the primary display is not attached to the main housing or is not displaying the graphical user interface, one or more of the following secondary commands are available for selection on the system status display and received from the system status display-and delivered to the ventilation control system:
   power save,
   primary display shut-down,
   system status display shut-down,
   breath-type change,
   pressure support change,
   oxygen percent change, and
   tidal volume change.

5. The ventilation system of claim 1 wherein:
   when the ventilation system is ventilating a patient and is receiving power from an internal power source and the primary display is not attached to the main housing or is not displaying the graphical user interface, one or more of the following secondary commands are received from the system status display and delivered to the ventilation control system:
   power save,
   primary display shut-down,
   breath-type change,
   pressure support change,
   oxygen percent change, and
   tidal volume change.

6. The ventilation system of claim 1 wherein:
   when the ventilation system is not ventilating a patient and is receiving power from an external power source and the primary display is not attached to the main housing or is not displaying the graphical user interface, one or more of the following secondary commands are received from the system status display and delivered to the ventilation control system:
   power save,
   primary display shut-down, and
   system status display shut-down.

7. The ventilation system of claim 1 wherein:
   when the ventilation system is not ventilating a patient and is receiving power from an internal power source and the primary display is not attached to the main housing or is not displaying the graphical user interface, one or more of the following secondary commands are received from the system status display and delivered to the ventilation control system:
power save,
primary display shut-down, and
system status display shut-down.

8. The ventilation system of claim 7 further comprising:
a control switch that turns on the system status display when the ventilation system is not ventilating the patient and is receiving power from the internal power source.

9. A method for controlling a ventilator system comprising:
ventilating a patient with a ventilator system comprising a system status display and a primary display removable from a main ventilator housing;
controlling the system status display with a ventilation control system, wherein the ventilation control system receives and executes user selected secondary commands from the system status display, wherein the secondary commands offered for selection by the system status display vary based at least on attachment of the primary display;
controlling the primary display with a primary display controller, wherein the primary display controller receives and executes user selected primary commands from a graphical user interface of the primary display; and
operating the system status display on less power than an amount of power necessary to operate the primary display.

10. The method of claim 9, further comprising:
determining that the ventilator system is receiving power from an external power source;
determining that the primary display is attached to the main housing and is displaying the graphical user interface; and
selecting to offer no secondary commands on the system status display based on the step of determining that the ventilator system is receiving power from the external power source and based on the step that the primary display is attached to the main housing and is displaying the graphical user interface.

11. The method of claim 9, further comprising:
determining that the ventilator system is receiving power from an external power source;
determining that the primary display is attached to the main housing and is displaying the graphical user interface; and
offering one or more of the following secondary commands on the system status display based on the step of determining that the ventilator system is receiving power from the external power source and based on the step of determining that the primary display is attached to the main housing and is displaying the graphical user interface:
power save,
primary display shut-down,
system status display shut-down,
breath-type change,
pressure support change,
oxygen percent change, and
tidal volume change.

12. The method of claim 9, further comprising:
determining that the ventilator system is receiving power from an external power source;
determining that the primary display is not attached to the main housing or is not displaying the graphical user interface; and
offering one or more of the following secondary commands on the system status display based on the step of determining that the ventilator system is receiving power from the external power source and based on the step of determining that the primary display is not attached to the main housing or is not displaying the graphical user interface:
power save,
primary display shut-down,
breath-type change,
pressure support change,
oxygen percent change, and
tidal volume change.

13. The method of claim 9, further comprising:
determining that the ventilator system is receiving power from an internal power source;
determining that the primary display is not attached to the main housing or is not displaying the graphical user interface; and
offering one or more of the following secondary commands on the system status display based on the step of determining that the ventilator system is receiving power from the internal power source and based on the step of determining that the primary display is not attached to the main housing or is not displaying the graphical user interface:
power save,
primary display shut-down,
breath-type change,
pressure support change,
oxygen percent change, and
tidal volume change.

14. The method of claim 9, further comprising utilizing less than 50% of power used by the primary display when in operation to power the system status display when in operation.

15. A method for controlling a ventilator system comprising:
controlling a system status display with a ventilation control system, wherein the ventilation control system receives and executes user selected secondary commands from the system status display, wherein the secondary commands offered for selection by the system status display vary based at least on attachment of a primary display;
controlling the primary display with a primary display controller, wherein the primary display controller receives and executes user selected primary commands from a graphical user interface of the primary display; and
operating a system status display on less power than an amount of power necessary to operate the primary display controller.

16. The method of claim 15, further comprising:
determining that the ventilator system is not ventilating a patient;
determining that the ventilator system is receiving power from an external power source;
determining that the primary display is not attached to a main housing or is not displaying the graphical user interface; and
offering one or more of the following secondary commands on the system status display based on the step of determining that the ventilator system is not ventilating the patient, based on the step of determining that the ventilator system is receiving power from the external power source, and based on the step of determining that the primary display is not attached to the main housing or is not displaying the graphical user interface:
power save,
primary display shut-down,
system status display shut-down,
ventilator status,
breath-type set-up,
pressure support set-up,
oxygen percent set-up, and
tidal volume set-up.

17. The method of claim 15, further comprising:
determining that the ventilator system is not ventilating a patient;
determining that the ventilator system is receiving power from an internal power source;
determining that the primary display is not attached to the main housing or is not displaying the graphical user interface; and
offering one or more of the following secondary commands on the system status display based on the step of determining that the ventilator system is not ventilating the patient, based on the step of determining that the ventilator system is receiving power from the internal power source, and based on the step of determining that the primary display is not attached to the main housing or is not displaying the graphical user interface:
power save,
primary display shut-down,
system status display shut-down,
breath-type set-up,
pressure support set-up,
oxygen percent set-up, and
tidal volume set-up.

18. A method for displaying ventilation information comprising:
ventilating a patient with a ventilation system comprising a system status display and a primary display removable from a main ventilator housing;
controlling the system status display with a ventilation control system;
controlling the primary display with a primary display controller;
determining that the primary display is removed from the main ventilator housing with the ventilation control system; and
based on the determining step, activating the system status display that runs on less power than an amount of power necessary to operate the primary display with the ventilation control system.

19. A method for displaying ventilation information comprising:
controlling a system status display with a ventilation control system;
controlling a removable primary display with a primary display controller;
determining that the primary display is removed from a main ventilator housing with the ventilation control system; and
based on the determining step, activating the system status display that runs on less power than an amount of power necessary to operate the primary display controller with the ventilation control system.

* * * * *